(12) United States Patent
Chopra et al.

(10) Patent No.: US 8,827,934 B2
(45) Date of Patent: Sep. 9, 2014

(54) METHOD AND SYSTEM FOR DETERMINING INFORMATION OF EXTREMA DURING EXPANSION AND CONTRACTION CYCLES OF AN OBJECT

(75) Inventors: Prashant Chopra, Sunnyvale, CA (US); Caitlin Q. Donhowe, Sunnyvale, CA (US); Vincent Duindam, Mountain View, CA (US); Giuseppe Maria Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 475 days.

(21) Appl. No.: 13/297,066

(22) Filed: Nov. 15, 2011

(65) Prior Publication Data
US 2012/0289843 A1 Nov. 15, 2012

Related U.S. Application Data

(63) Continuation-in-part of application No. 13/107,562, filed on May 13, 2011.

(51) Int. Cl.
*A61B 5/00* (2006.01)

(52) U.S. Cl.
USPC .......................................................... 600/593

(58) Field of Classification Search
USPC ........................................ 600/534, 587, 593
See application file for complete search history.

(56) References Cited

U.S. PATENT DOCUMENTS

| | | | |
|---|---|---|---|
| 5,765,561 A | 6/1998 | Chen et al. | |
| 5,797,849 A | 8/1998 | Vesely et al. | |
| 6,246,898 B1 | 6/2001 | Vesely et al. | |
| 6,256,090 B1 | 7/2001 | Chen et al. | |
| 6,346,940 B1 | 2/2002 | Fukunaga | |
| 6,468,265 B1 | 10/2002 | Evans et al. | |
| 6,522,906 B1 | 2/2003 | Salisbury, Jr. et al. | |
| 6,923,768 B2 | 8/2005 | Camus et al. | |
| 7,233,820 B2 | 6/2007 | Gilboa | |
| 7,398,116 B2 | 7/2008 | Edwards | |

(Continued)

FOREIGN PATENT DOCUMENTS

| | | |
|---|---|---|
| EP | 1779779 A3 | 9/2007 |
| EP | 2286714 A3 | 3/2012 |
| WO | 2008125910 A2 | 10/2008 |

OTHER PUBLICATIONS

International Search Report and Written Opinion for Application No. PCT/US2012/065165, mailed on Feb. 8, 2013, 9 pages.

(Continued)

*Primary Examiner* — Max Hindenburg

(57) ABSTRACT

A medical system provides navigation assistance to a surgeon for navigating a flexible medical device through linked passages of an anatomical structure to a target area. For tracking, navigation, and other purposes, information of extrema is determined during expansion and contraction cycles of an object by receiving time sampled information from sensors distributed along a length of a flexible device so as to indicate the shape of the device over time while the device extends through a lumen of the object so as to conform to and resemble the shape of the lumen, displacements over time of a selected point at a selected insertion length of the flexible device into the lumen of the object relative to a reference point are determined, extrema time points are determined by identifying sign changes of the slope of the determined displacements over time, and extrema types are determined using extrema type characteristics.

42 Claims, 18 Drawing Sheets

(56) References Cited

U.S. PATENT DOCUMENTS

| | | |
|---|---|---|
| 7,517,320 B2 | 4/2009 | Wibowo et al. |
| 7,756,563 B2 | 7/2010 | Higgins et al. |
| 7,773,792 B2 * | 8/2010 | Kimmel et al. ............... 382/128 |
| 7,889,905 B2 | 2/2011 | Higgins et al. |
| 7,901,348 B2 | 3/2011 | Soper et al. |
| 8,500,660 B2 * | 8/2013 | Buchwald et al. ............ 600/593 |
| 8,521,249 B2 * | 8/2013 | O'Dea ........................... 600/373 |
| 8,657,757 B2 * | 2/2014 | Lazar et al. .................... 600/538 |
| 2002/0087169 A1 | 7/2002 | Brock et al. |
| 2003/0055410 A1 | 3/2003 | Evans et al. |
| 2003/0220541 A1 | 11/2003 | Salisbury, Jr. et al. |
| 2004/0097806 A1 | 5/2004 | Hunter et al. |
| 2005/0107679 A1 | 5/2005 | Geiger et al. |
| 2005/0182295 A1 | 8/2005 | Soper et al. |
| 2005/0182319 A1 | 8/2005 | Glossop |
| 2005/0197559 A1 | 9/2005 | Boese et al. |
| 2005/0200324 A1 | 9/2005 | Guthart et al. |
| 2005/0261550 A1 | 11/2005 | Akimoto et al. |
| 2006/0058647 A1 | 3/2006 | Strommer et al. |
| 2006/0184016 A1 | 8/2006 | Glossop |
| 2006/0195033 A1 | 8/2006 | Akimoto et al. |
| 2006/0202998 A1 | 9/2006 | Hirakawa et al. |
| 2007/0010743 A1 | 1/2007 | Arai |
| 2007/0135803 A1 | 6/2007 | Belson |
| 2007/0293721 A1 | 12/2007 | Gilboa |
| 2008/0118135 A1 | 5/2008 | Averbuch et al. |
| 2008/0262297 A1 | 10/2008 | Gilboa et al. |
| 2009/0123111 A1 | 5/2009 | Udd |
| 2009/0137952 A1 | 5/2009 | Ramamurthy et al. |
| 2009/0149703 A1 | 6/2009 | Tanaka |
| 2009/0163800 A1 | 6/2009 | Xu et al. |
| 2009/0292166 A1 | 11/2009 | Ito et al. |
| 2010/0152600 A1 | 6/2010 | Droitcour et al. |
| 2010/0234857 A1 | 9/2010 | Itkowitz et al. |
| 2010/0249506 A1 | 9/2010 | Prisco |
| 2010/0249507 A1 * | 9/2010 | Prisco et al. .................. 600/117 |
| 2010/0256558 A1 | 10/2010 | Olson et al. |
| 2010/0286548 A1 | 11/2010 | Lazar et al. |
| 2010/0295931 A1 | 11/2010 | Schmidt |
| 2011/0015648 A1 | 1/2011 | Alvarez et al. |
| 2011/0040404 A1 | 2/2011 | Diolaiti et al. |
| 2012/0289777 A1 | 11/2012 | Chopra et al. |

OTHER PUBLICATIONS

Banovac, Filip et al., "Liver Tumor Biopsy in a Respiring Phantom with the Assistance of a Novel Electromagnetic Navigation Device," 2002, pp. 200-207, Springer-Verlag.

Burschka, Darius et al., "Navigating Inner Space: 3-D Assistance for Minimally Invasive Surgery," Robotics and Autonomous Systems, 2005, pp. 5-26, vol. 52—Issue 1, Elsevier.

Chiu, Adeline M. et al., "3-D Image Guidance for Minimally Invasive Robotic Coronary Artery Bypass," The Heart Surgery Forum, Jun. 8, 2000, vol. 3—No. 3, pp. 224-231.

Coste-Maniere; Eve et al., "Optimal Planning of Robotically Assisted Heart Surgery: First Results on the Transfer Precision in the Operating Room," The International Journal of Robotics Research, 2004, pp. 539-548, vol. 23,—Issue 4-5, SAGE Publications.

Doignon, C. et al., "Model-based 3-D pose estimation and feature tracking for robot assisted surgery with medical imaging," published in "From Features to Actions: Unifying Perspectives in Computational and Robot Vision" workshop at the IEEE International Conference on Robotics and Automation, Apr. 2007, 10 pages. Internet: http://hal.archives-ouvertes.fr/docs/00/35/06/47/PDF/2007 wkicra doignon.pdf.

Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-450, vol. 2, Springer Verlag.

Proceedings of Medicine Meets Virtual Reality II: Interactive Technology & Healthcare: Visionary Applications for Simulation Visualization Robotics, 1994, Elsevier, 275 Total Pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Search Report and Written Opinion for Application No. PCT/US2012/035390, mailed on Nov. 14, 2012, 11 pages.

\* cited by examiner

METHOD AND SYSTEM FOR DETERMINING INFORMATION OF EXTREMA DURING EXPANSION AND CONTRACTION CYCLES OF AN OBJECT

CROSS REFERENCE TO RELATED APPLICATIONS

This application is a continuation-in-part of U.S. application Ser. No. 13/107,562 filed May 13, 2011 entitled "Medical System Providing Dynamic Registration of a Model of an Anatomical Structure for Image-Guided Surgery", which is incorporated herein by reference.

FIELD OF THE INVENTION

The present invention generally relates to monitoring periodic expansions and contractions of an object and in particular, to a method and system for determining information of extrema during expansion and contraction cycles of an object for image guided surgery and other applications.

BACKGROUND

Image guided surgery helps surgeons navigate medical devices to targets in patients so that therapeutic and/or diagnostic medical procedures may be performed on the targets. For guidance, the pose (i.e., position and orientation) of a working end of a medical device may be tracked and its image displayed along with or superimposed on a model of an anatomical structure associated with the target. The model may be computer generated from pre-operative and/or intra-operative patient anatomy scan data such as x-ray, ultrasound, fluoroscopy, computed tomography (CT), magnetic resonance imaging (MRI), and other imaging technologies. The medical device may be an endoscope, catheter, or medical instrument that has a steerable tip and flexible body capable of conforming to body passages leading to the target in an anatomical structure of the patient.

Displaying the target upon which the therapeutic and/or diagnostic medical procedure is to be performed, the model of the anatomical structure in which the target resides or is adjacent to, and an image of the working end of the medical device superimposed on the model of the anatomical structure may be particularly useful to the surgeon to provide assistance in guiding the medical device through natural and/or artificial body passages to and through the anatomical structure to the target. Proper registration of the model to the medical device, however, may be very difficult when the anatomical structure is neither immobile nor rigid, but instead, moves and/or changes shape according to periodic or non-periodic movement of the anatomical structure such as the case with a patient's lung or beating heart.

OBJECTS AND SUMMARY

Accordingly, one object of one or more aspects of the present invention is a system and method implemented therein that are useful for providing dynamic registration of a model of an anatomical structure with intra-operative anatomical information for image-guided surgery.

Another object of one or more aspects of the present invention is a system and method implemented therein that are simple to implement and do not require additional hardware components for identifying extrema types and determining extrema time points during expansion and contraction cycles of an object.

Another object of one or more aspects of the present invention is a medical system and method implemented therein that are computationally efficient and suitable for real-time applications for identifying extrema types and determining extrema time points during expansion and contraction cycles of an object.

Another object of one or more aspects of the present invention is a medical system and method implemented therein that provide accurate and/or reliable results for identifying extrema types and determining extrema time points during expansion and contraction cycles of an object.

These and additional objects are accomplished by the various aspects of the present invention, wherein briefly stated, one aspect is a method for determining information of extrema during expansion and contraction cycles of an object, the method comprising: receiving time sampled information from a plurality of sensors distributed along a length of a flexible device so as to indicate the shape of the flexible device over time while the flexible device extends through a lumen of the object so as to conform to and resemble the shape of the lumen; determining displacements over time of a selected point at a selected insertion length of the flexible device into the lumen of the object relative to a reference point using the time sampled information received from the plurality of sensors; determining extrema time points during the expansion and contraction cycles of the object by identifying sign changes of the slope of the determined displacements of the point of the lumen over time; and identifying extrema types during the expansion and contraction cycles of the object by using extrema type characteristics.

Another aspect is a system comprising: a flexible device including a plurality of sensors distributed along a length of the flexible device so as to indicate the shape of the flexible device as the flexible device extends through a lumen of an object so as to conform to and resemble the shape of the lumen; and one or more processors adapted to determine information of extrema during expansion and contraction cycles of the object by receiving time sampled information from the plurality of sensors, determine displacements over time of a selected point at a selected insertion length of the flexible device into the lumen of the object relative to a reference point using the time sampled information received from the plurality of sensors, determine the extrema time points during the expansion and contraction of the object over time by identifying changes in the sign of the slope of the determined displacements of the point over time, and identify extrema types during the expansion and contraction cycles of the object by using extrema type characteristics.

Additional objects, features and advantages of the various aspects of the present invention will become apparent from the following description which should be taken in conjunction with the accompanying drawings.

DETAILED DESCRIPTION

Figure 1:
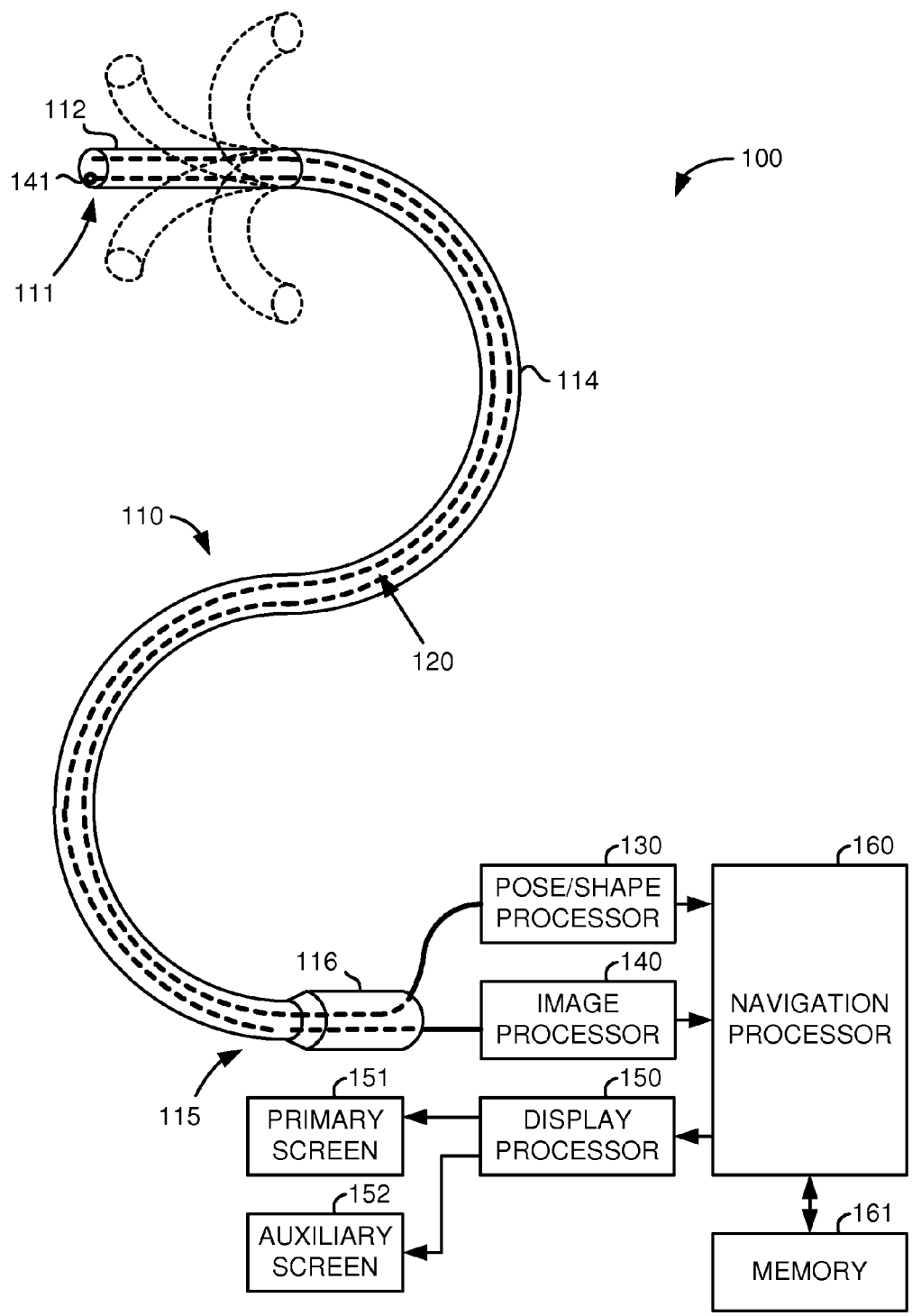
FIG. 1 illustrates a medical system, utilizing aspects of the present invention, which includes a hand-operated medical device.

FIG. 1 illustrates, as an example, a medical system 100 including a steerable medical device 110, one or more fiber optic cables 120 inserted in the medical device 110, a pose/shape processor 130, an image processor 140, an image capturing element 141, a display processor 150, a primary display screen 151, an auxiliary display screen 152, a navigation processor 160, and memory 161. Although shown as separate units, the pose/shape processor 130, image processor 140, display processor 150, and navigation processor 160 may each be implemented as hardware, firmware, software or a combination thereof, which interact with or are otherwise executed by one or more computer processors. The primary and auxiliary display screens, 151 and 152, are preferably computer monitors capable of displaying three-dimensional images to an operator of the system 100. However, for cost considerations, either or both of the primary and auxiliary display screens, 151 and 152, may be a standard computer monitor capable of only displaying two-dimensional images.

The medical device 110 has a flexible body 114, a steerable tip 112 at its distal end 111, and a hand-operable handle 116 at its proximal end 115. Control cables (not shown) or other control means typically extend from the handle 116 to the steerable tip 112 so that the tip 112 may be controllably bent or turned as shown for example by dotted line versions of the bent tip 112. The medical device 110 may be an endoscope, catheter or other medical instrument having a flexible body and steerable tip.

The image capturing element 141 may be a stereoscopic or monoscopic camera disposed at the distal end 111 for capturing images that are transmitted to and processed by the image processor 140 and/or display processor 150 and displayed on the primary display screen 151, auxiliary display screen 152, and/or other display means according to the various aspects of the invention as described herein. Alternatively, the image capturing element 141 may be a coherent fiber-optic bundle that couples to an imaging and processing system on the proximal end of the medical device 110, such as a fiberscope. The image capturing element 141 may also be single or multi-spectral that captures image data in the visible or infrared/ultraviolet spectrum. Thus, any image capturing element, device, or system referred to herein may be any one or a combination of these and other imaging technologies. One of a plurality of fiber optic cables 120 may be coupled at its proximal end to a light source (not shown) for illumination purposes at the distal end 111. Others of the fiber optic cables 120 may be configured with position and bend or shape sensors such as Fiber Bragg Gratings (or other strain sensors such as those employing Rayleigh scattering) distributed along the length of the medical device 110 so that light passing through the fiber optic cable is processed by the pose/shape processor 130 to determine a current pose and shape of the medical device 110.

Figure 2:
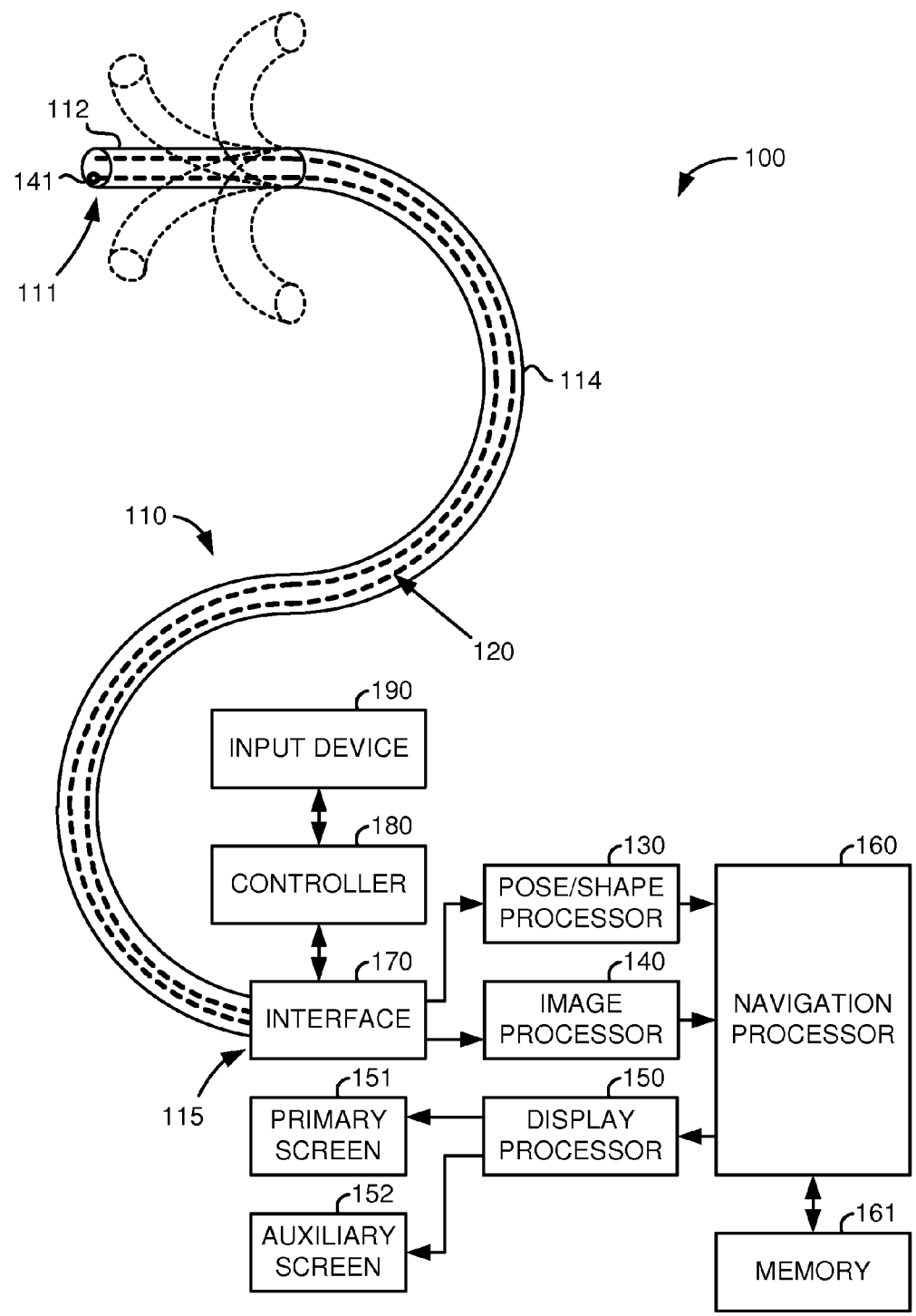
FIG. 2 illustrates an alternative medical system, utilizing aspects of the present invention, which includes a teleoperated medical device.

FIG. 2 illustrates, as an example, an alternative embodiment of the medical system 100 in which the handle 116 is replaced by an electromechanical interface 170, controller 180, and input device 190 for teleoperating the medical device 110. The interface 170 includes actuators for actuating cables in the medical device 110 to steer its tip 112 as well as an actuator for moving the entire medical device 110 forward and backward so that it may be inserted into and retracted out of a patient through an entry port such as a natural body orifice or a surgeon created one. The controller 180 is preferably implemented as hardware, firmware or software (or a combination thereof) in the same one or more computer processors as the processors 130, 140, 150, and 160, or a different computer processor. The flexible body 114 may be passively or actively bendable in this embodiment.

Examples of such steerable medical devices are described in U.S. 2010/0249506 A1 entitled "Method and System for Assisting an Operator in Endoscopic Navigation" and WO 2009/097461 A1 entitled "Apparatus and Methods for Automatically Controlling an Endoscope, which are each incorporated herein by reference. Details on the determination of the endoscope's position and bending using Fiber Bragg Gratings may be found, for examples, in U.S. 2007/0156019 A1 entitled "Robotic Surgery System Including Position Sensors Using Fiber Bragg Gratings", U.S. 2008/0212082 A1 entitled "Fiber Optic Position and/or Shape Sensing Based on Rayleigh Scatter", U.S. 2008/0218770 A1 entitled "Robotic Surgical Instrument and Methods using Bragg Fiber Sensors", and U.S. 2009/0324161 A1 entitled "Fiber Optic Shape Sensor", which are each incorporated herein by reference.

Figure 3:
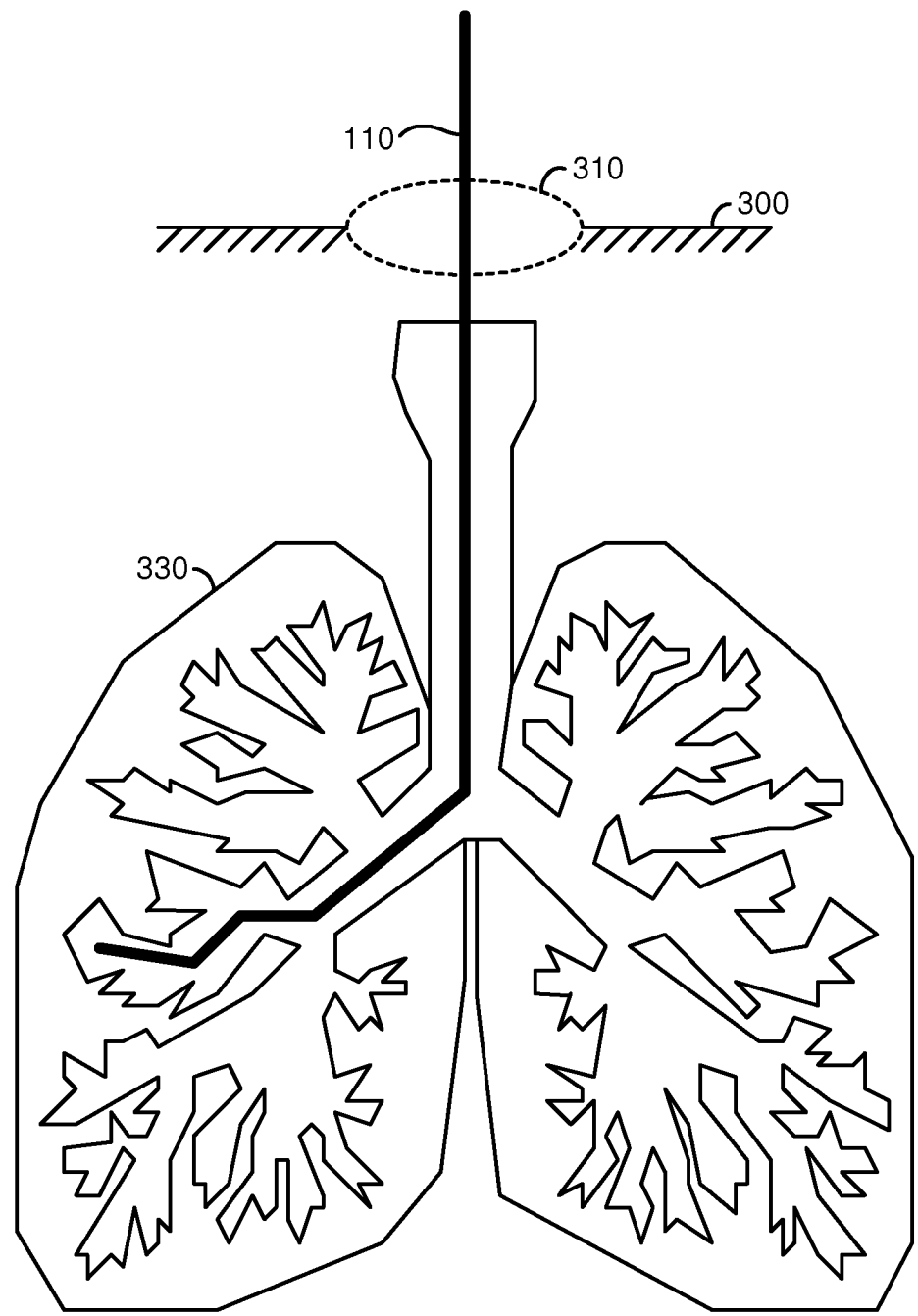
FIG. 3 illustrates a diagram of a medical device inserted into an anatomical structure of a patient.

FIG. 3 illustrates, as an example, a diagram of a medical device 110 inserted through an entry port 310 and extending into an anatomical structure 330 of a patient 300. In this example, the anatomical structure 330 is a pair of lungs having a plurality of natural body passages including a trachea, bronchi, and bronchioles; the entry port 310 is the patient's mouth; and the medical device 110 is a bronchoscope. Due to the nature of the lung, the medical device 110 may be guided through a number of linked passages of the bronchial tree. In doing so, the flexible body 114 of the medical device 110 conforms to the passages through which it travels. Although a pair of lungs is shown in the present example, it is to be appreciated that the various aspects of the present invention are also applicable and useful for other anatomical structures such as the heart, brain, digestive system, circulatory system, and urinary system, in addition to the respiratory system. Further, although only natural body passages are shown, the methods described herein are also applicable to artificial or surgeon created passages (i.e., artificial passages) that may be formed during or prior to a medical procedure and superimposed on the computer model of the patient anatomy.

Figure 4:
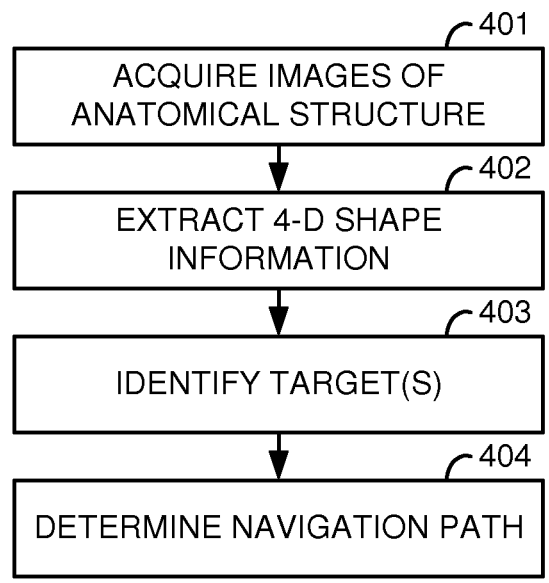
FIG. 4 illustrates a flow diagram of preoperative tasks conducted prior to performing a medical procedure on a patient.

FIG. 4 illustrates, as an example, a flow diagram of preoperative tasks that are performed in preparation for a medical procedure on a patient. In the following example, the anatomical structure is presumed to be one that moves during a medical procedure in an identifiable way such as periodic motion of the air and blood circulatory systems or a non-periodic motion such as a body response to a stimulus. Although aspects of the invention may still be applicable and useful when the anatomical structure does not move during a medical procedure, the full advantages of the present invention are best experienced in an environment in which the anatomical structure moves in an identifiable or otherwise known manner during the medical procedure.

In block 401, one or more sets of images of a patient is acquired using an appropriate imaging technology from which a set of three-dimensional (3-D) computer models of the anatomical structure may be generated, wherein each 3-D computer model is associated with a different point in time over a period of time so that time represents a fourth dimension and the images are referred to herein as four-dimensional (4-D) images. Additional dimensions may also be defined and used in the methods described herein. Examples of such an imaging technology include, but are not limited to, fluoroscopy, Magnetic Resonance Imaging, thermography, tomography, ultrasound, Optical Coherence Tomography, Thermal Imaging, Impedance Imaging, Laser Imaging, nano-tube X-ray imaging, etc.

The period of time over which images are captured depends upon the anatomical structure and the motion of interest. For example, when the anatomical structure is the lungs, one set of images may be for a periodic motion such as a respiratory cycle shown in FIG. 5 where the lung expands from a maximum exhalation state 501 (solid lines) to a maximum inhalation state 502 (dotted lines). Another set of images may be for a non-periodic motion such as a cough or other body reaction to a stimulus resulting in movement of the lungs. As another example, when the anatomical structure is the heart, one set of images may be for a periodic motion such as a blood circulatory cycle. The sampling rate which determines the number of such 3-D computer models is chosen so that the movement of the anatomical structure during such period of motion is adequately described for accurate registration and navigation purposes.

In block 402, 4-D shape information is extracted from the acquired images of the anatomical structure. When the acquired images are sets of two-dimensional (2-D) slices of the anatomical structure sampled at incremental points in time (e.g., according to a sampling rate) over the period of motion, 3-D shape information for the anatomical structure is generated for each set of 2-D slices corresponding to the same point in time. Thus, for n-points in time, "n" sets of 3-D shape information are extracted, where "n" is the number of sampling points in time over the period of motion.

In block 403, one or more targets are identified in the anatomical structure. The targets are locations or objects in or adjacent to the anatomical structure where or upon which a medical procedure is to be performed. For example, the target may be a tumor in or adjacent to the anatomical structure. The target(s) may be identified by a surgeon in a conventional manner by analysis of the acquired images of the anatomical structure or the extracted 4-D shape information, whichever is more convenient and/or reliable for such identification.

In block 404, a navigational path is determined to and through the anatomical structure for the working end of the medical device 110 to travel to each target. In this case, the working end is assumed to be the distal end 111 of the medical device 110. The surgeon may determine a suitable navigational path to a target by analyzing the acquired images of the anatomical structure or the extracted 4-D shape information so as to take into account any damage to the patient that the medical device 110 may cause as it moves towards the target as well as the shortest time and/or shortest path. Alternatively, a computer program may cause a processor to perform such analysis to determine the navigational path using artificial intelligence techniques.

Figure 6:
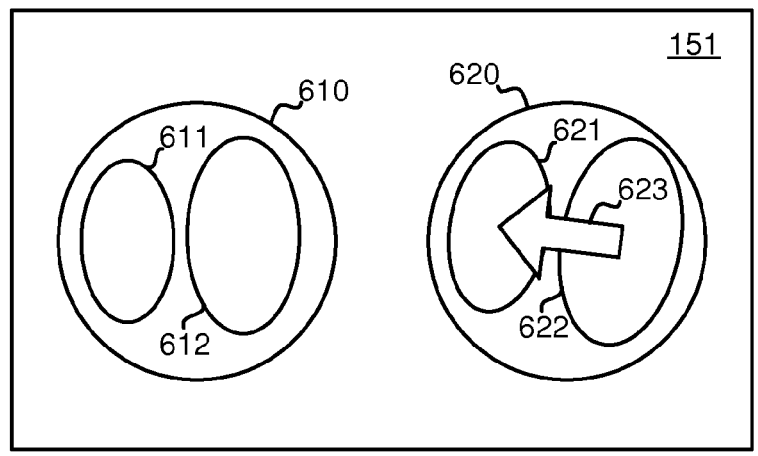
FIG. 6 illustrates a view of a primary screen during navigation of a medical device to a target area in an anatomical structure before registration of a computer model of the anatomical structure to the medical device.

FIG. 6 illustrates, as an example, a view of the primary screen 151 during navigation of the medical device 110 to a target area in an anatomical structure before registration of a computer model of the anatomical structure to the medical device. A left image 610 is the image captured by the image capturing element 141 while viewing a bifurcation in a lung, wherein the bifurcation indicates a left passage 611 and a right passage 612 through which one or the other the medical device 110 may pass through as it is inserted further into the lung. Also shown is a right image 620 which is a virtual image generated by a virtual camera viewing a corresponding location in a 4-D computer model of the anatomical structure which has been generated from the 4-D shape information extracted in block 402 of FIG. 4 before the 4-D computer model is registered in some fashion to the medical device 110. In particular, although left 621 and right 622 passages corresponding to the passages 611 and 612 are shown, their sizes and alignments differ due to translational and rotational errors in the registration transformation relating the 4-D computer model of the anatomical structure to the medical device 110.

Figure 7:
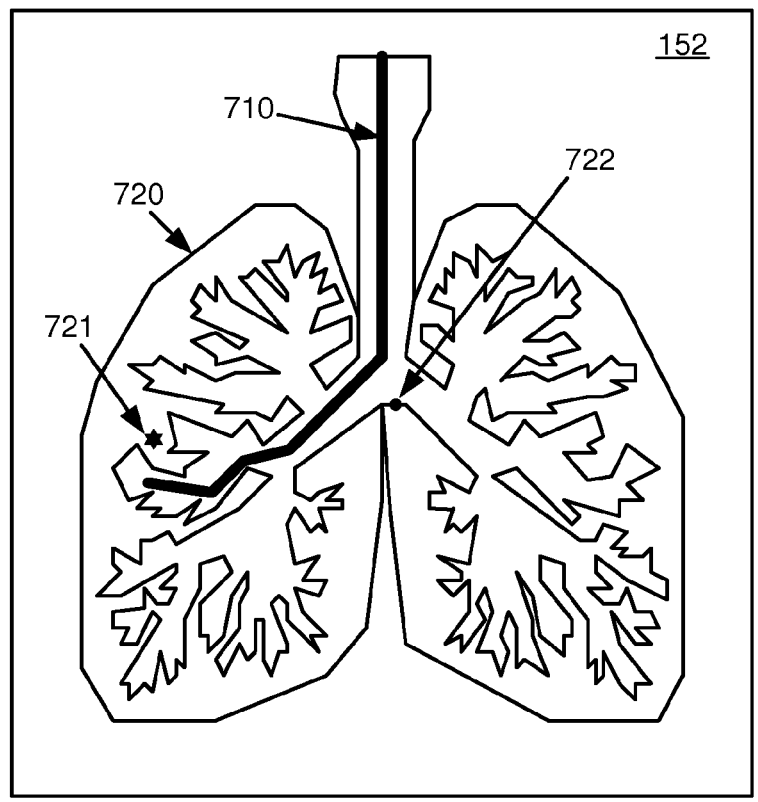
FIG. 7 illustrates a view of an auxiliary screen during navigation of a medical device to a target area in an anatomical structure.

FIG. 7 illustrates, as an example, a view of the auxiliary screen 152 during navigation of the medical device 110 to a target area in an anatomical structure. The view may be either a 2-D or 3-D view of a computer model 720 of the anatomical structure 330 and a computer model 710 of the medical device 110, which is updated in real-time as the medical device 110 moves through the anatomical structure 330. Also shown is an indication 721 of the target. Thus, the auxiliary screen 152 assists the surgeon to steer the medical device 110 through the anatomical structure 330 to the target.

Figure 8:
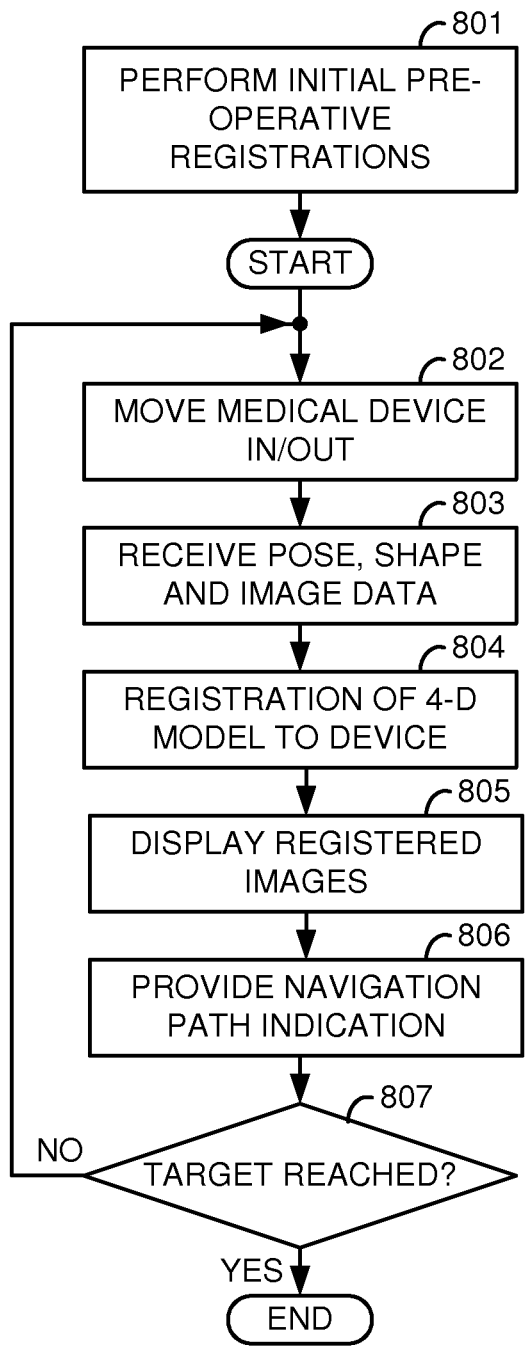
FIG. 8 illustrates a flow diagram of a method for performing a medical procedure including one of a first and second method, utilizing aspects of the present invention, for registering a computer model of an anatomical structure with a medical device.

FIG. 8 illustrates, as an example, a flow diagram of a method for performing a medical procedure on a patient. In block 801, a number of pre-operative tasks are performed in preparation of performing the medical procedure. First, the medical device 110 is localized to a fixed reference frame in a conventional manner by, for example, touching the distal end 111 of the medical device 110 to a known and stationary point in the fixed reference frame. Second, the patient may be registered to the fixed reference frame in a conventional manner by touching and holding the distal end 111 of the medical device 110 to one or more points on the patient, which points correspond to identifiable points on the acquired images of the patient as described in block 401 of FIG. 4, during the period of motion associated with the 4-D computer model. Thus, by applying known relationships between the one or more points on the patient to the anatomical structure 330, the computer model of the anatomical structure may be registered to the anatomical structure of the patient, the fixed reference frame, and the medical device 110.

Navigation of the medical device 110 through the linked passages of the anatomical structure 330 to the target is performed from START to END in FIG. 8. In block 802, the medical device 110 is moved through the linked passages in either the insertion or retraction direction by the surgeon either manipulating the handle 116 or the input device 190, depending upon the embodiment of the medical system 100 being used by the surgeon. In block 803, the navigation processor 160 receives pose and shape information for the medical device 110 from the pose/shape processor 130 and image data from the image processor 140. Thus, the navigation processor 160 has information on the current position and orientation (i.e., pose) of the distal end 111 of the medical device 110 and the shape of the flexible body 114 of the medical device 110 along with an image that has been captured by the image capturing element 141 at that time.

In block 804, the navigation processor 160 performs a correction to the registration of the 4-D computer model of the anatomical structure 330 to the medical device 110. One method for performing this registration is described in reference to FIG. 9 and another method is described in reference to FIG. 10. Alternatively, rather than performing one or the other of the two methods, both methods may be performed as shown and described in reference to FIG. 11. In performing block 804, it is assumed that the shape of the medical device 110 conforms to the shape of the passage of the anatomical structure in which the medical device 110 is disposed at the time. Therefore, registration of the computer model to the medical device 110 effectively registers the computer model of the anatomical structure to the actual anatomical structure of the patient.

Figure 14:
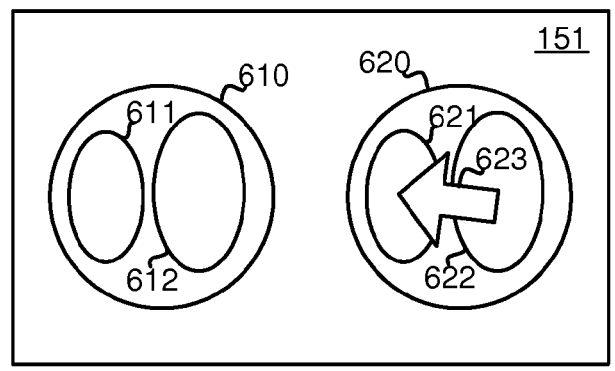
FIG. 14 illustrates a view of a primary screen during navigation of a medical device to a target area in an anatomical structure after registration of a computer model of the anatomical structure to the medical device.

In block 805, the captured image and virtual image are displayed in a similar manner as shown and described in reference to FIG. 6 except that the virtual image 620 is now adjusted to resemble that of the captured image 610, such as shown in FIG. 14, due to the proper registration of the 4-D computer model of the anatomy 330 to the medical device 110. In particular, the size and orientations of the left and right passages, 621 and 622, of the virtual image 620 match those of the left and right passages, 611 and 612, of the captured image 610. In block 806, a navigational path indication such as the arrow 623 in the virtual image 620 is provided so that the surgeon knows that the medical device 110 is to be steered into the indicated passage.

In block 807, a determination is made whether the working end 111 of the medical device 110 has come within a threshold distance to the target. The threshold distance in this case is a distance that is sufficient so that the working end 111 of the medical device 110 can be manipulated by the surgeon to perform its intended purpose without requiring further insertion of the medical device 110 into the anatomical structure 330. If the determination in 807 is YES, then the guided navigation to the target is completed and the method ends. On the other hand, if the medical device 110 has not reached the threshold distance to the target, then the method jumps back to 802 so that the medical device 110 is moved further through the linked passages by the surgeon either manipulating the handle 116 or the input device 190, depending upon the embodiment of the medical system 100 being used by the surgeon.

Figure 9:
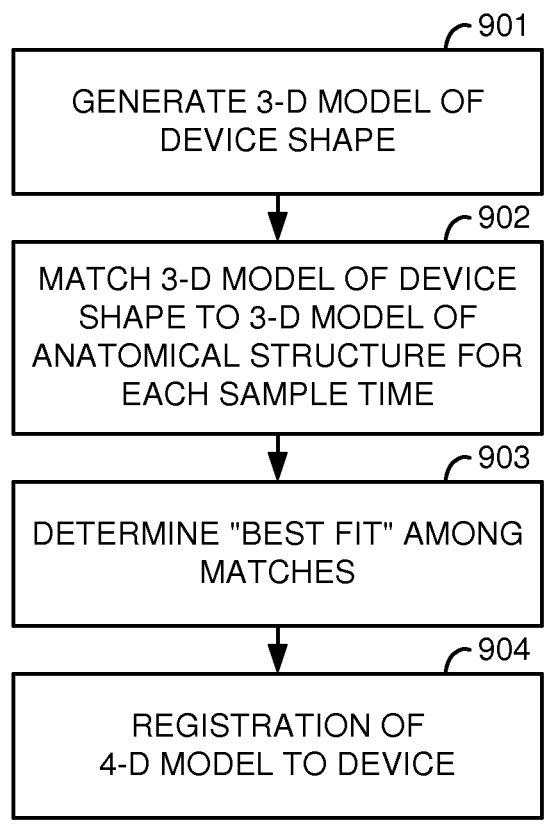
FIG. 9 illustrates a flow diagram of a first method, utilizing aspects of the present invention, for registering a computer model of an anatomical structure with a medical device.

FIG. 9 illustrates, as an example, a flow diagram of a first method (referred to as "shape registration") performable by the navigation processor 160 for registering a computer model of an anatomical structure with a medical device. This method is particularly useful when real-time images are unavailable from the perspective of the distal end 111 of the medical device 110, such as when the image capturing element 141 is either removed or its view is obstructed.

Figure 12A:
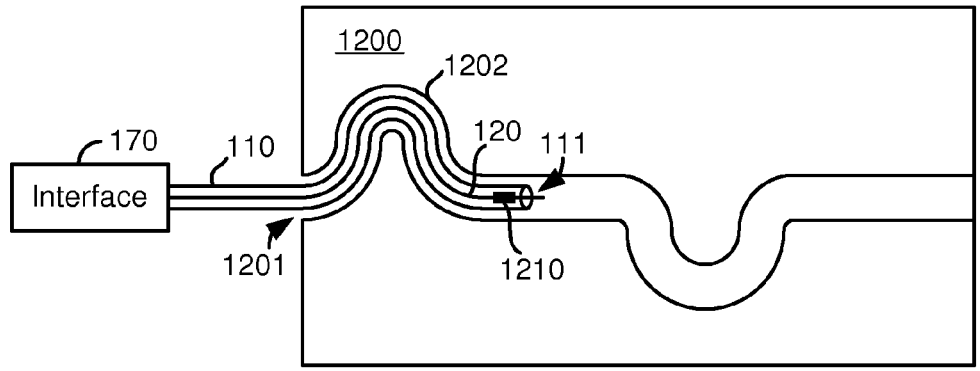
FIGS. 12A-C illustrate schematic drawings of a medical device having a single end sensor respectively at three different points in time as the medical device moves through a passage of an anatomical structure in a patient.
Figure 12B:
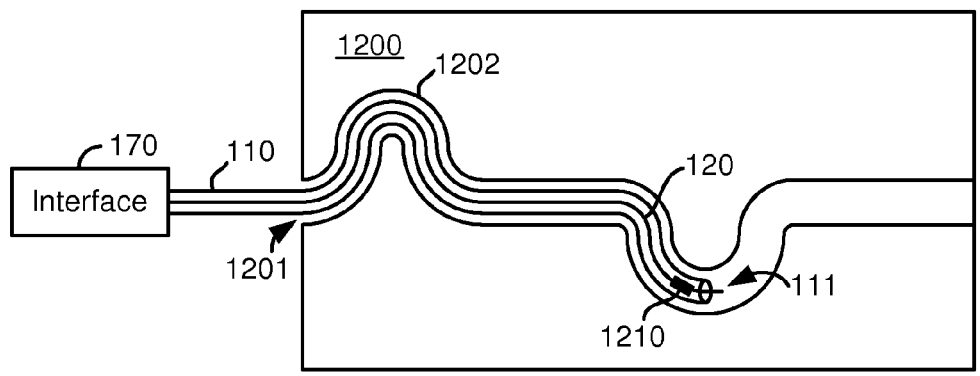
Figure 12C:
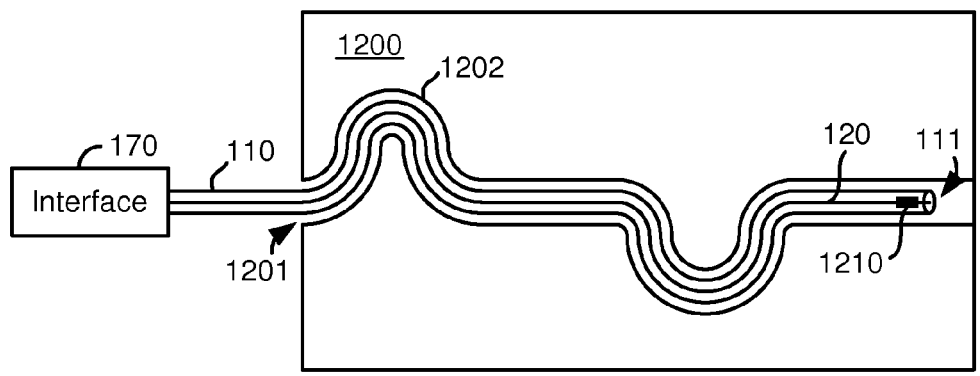
Figure 13:
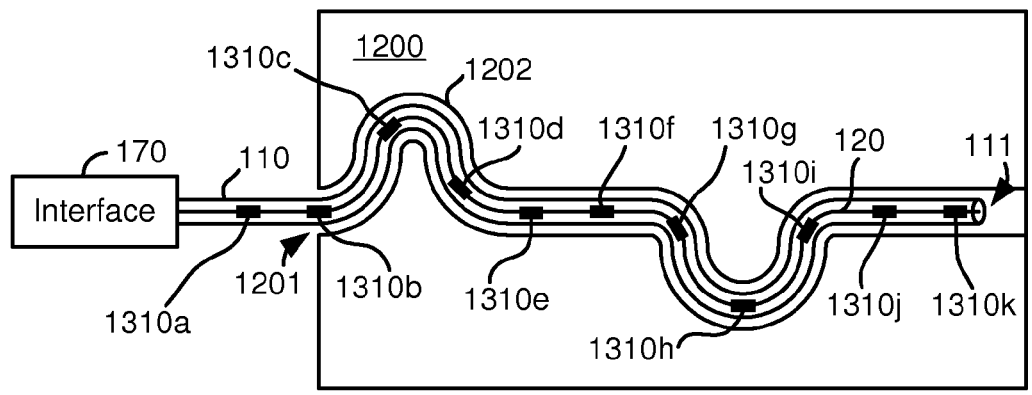
FIG. 13 illustrates a schematic drawing of a medical device having a plurality of distributed sensors at a single point in time while the medical device is disposed in a passage of an anatomical structure in a patient.

As previously explained, since the flexible body 114 conforms to the shape of the passage of the anatomical structure through which the medical device 110 is passing through at the time, the shape of the medical device 110 resembles that of the passage. Thus, by registering the computer model of the anatomical structure to the medical device 110, this is effectively the same as registering the computer model of the anatomical structure to the actual anatomical structure. Alternatively, the shape of the passage might be determined using an approach as described in reference to FIGS. 12A-C, where the pose of a distal end sensor 1210 is recorded at different points in time as the medical device 110 moves through the passage 1202 of an anatomical structure 1200. One problem with this approach, however, is that when the anatomical structure 1200 is moving, the different position measurements which are made at different points in time (and possibly different points in the dynamic movement of the anatomical structure), can lead to errors or complicated correctional adjustments. Therefore, a preferred embodiment of the present invention is shown in FIG. 13, where a plurality of sensors 1310*a*-1310*k* are employed that are sufficient in number and properly distributed along the length of the medical device 110 so that all pose and shape measurements may be accurately made at the same point in time.

In block 901, a 3-D computer model corresponding to the current pose and shape of the medical device 110 is generated using the pose and shape information received from the pose/shape processor 130. Since the pose and shape information is readily generated from position and shape sensors disposed in the medical device 110, a computationally fast determination of the medical device's pose and shape is made.

In block 902, the shape of the medical device 110 is compared against shapes of the linked passages in the 3-D computer model for each sampled point in time to find a closest match of linked passages. A number of well-known matching techniques may be used to perform this function such as an Iterative Closest Point (ICP) algorithm or a Singular Value Decomposition (SVD) algorithm as described, for example, in U.S. 2005/0182319 A1, which is incorporated herein by reference. Thus, for each sample time in a dynamic motion cycle, a closest match of the current shape of the medical device 110 (and consequently the passage in which it is disposed at the time) and one of the linked passages in a computer model of the anatomical structure is determined.

In block 903, deviations are determined between each closest match of linked passages determined in 902 and the shape of the medical device 110. The closest match of linked passages having the smallest deviation with the current shape of the medical device 110 is then determined to be the "best fit" among the matches. Thus, whereas block 902 determines for each 3-D computer model, the closest match between one or more of its passages with the current shape of the medical device, block 903 determines the 3-D computer model whose closest match of linked passages is the "best fit" (i.e., closest match) of the closest matches of all the 3-D computer models. In block 904, the "best fit" of linked passages in the 4-D computer model of the anatomical structure is then localized to the portion of the medical device 110 which it has been determined to be the "best fit" so that the 4-D computer model is registered to the medical device 110 (and consequently, the anatomical structure of the patient).

Figure 10:
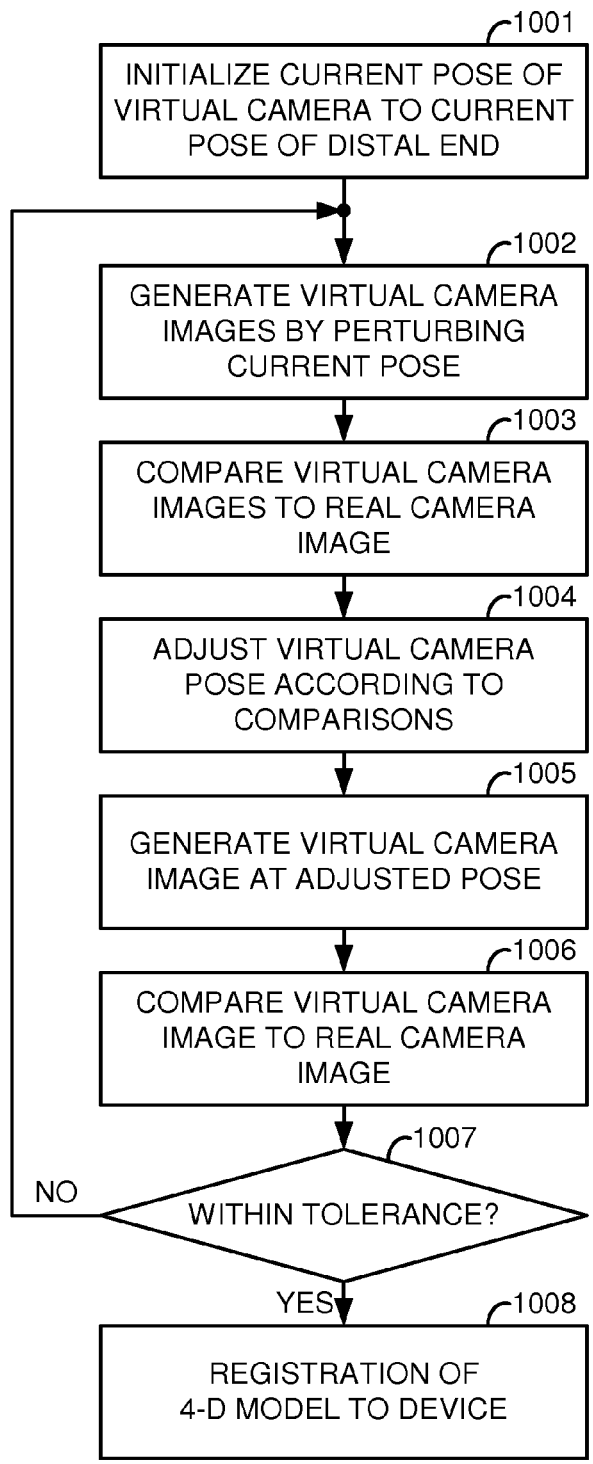
FIG. 10 illustrates a flow diagram of a second method, utilizing aspects of the present invention, for registering a computer model of an anatomical structure with a medical device.

FIG. 10 illustrates, as an example, a flow diagram of a second method (referred to as "virtual camera registration") performable by the navigation processor 160 for correcting the registration of a computer model of an anatomical structure with a medical device. In performing the method, it is assumed that a prior registration of the 4-D computer model and the medical device 110 has been performed (such as initially in block 801 of FIG. 8).

In block 1001, a virtual camera is initially assumed to be disposed at the current pose of the distal end of the medical device 110. In block 1002, one or more virtual images of the 4-D computer model of the anatomic structure are generated as though being captured by the virtual camera by perturbing the current pose of the virtual camera translationally and/or orientationally. In block 1003, the one or more virtual images are compared with the current image of the anatomical structure captured by the image capturing element 141. In block 1004, the virtual camera pose is adjusted according to the comparisons performed in block 1003 so that a virtual image captured by the virtual camera at the adjusted pose will better match the current image of the anatomical structure captured by the image capturing element 141. In block 1005, a virtual image of the 4-D computer model is generated as though being captured by the virtual camera at the adjusted pose. In block 1006, the virtual image captured by the virtual camera at the adjusted pose is compared to the current image of the anatomical structure captured by the image capturing element 141. In block 1007, a determination is made whether the deviation between the virtual image and the real captured image is within a tolerance range. The tolerance range may be pre-set to limit values previously determined in some fashion to result in acceptable matches within a reasonable time period. Alternatively, an algorithm may be used to incrementally change an initial tolerance range as a function of the results of the processing through the loop of blocks 1002-1007.

If the determination is YES, then in block 1008, the adjusted pose of the virtual camera is used to generate a registration transform to register the 4-D computer model of the anatomical structure to the medical device 110 and the registration transform is used to localize the 4-D computer model to the medical device 110. On the other hand, if the determination is NO, then the method jumps back to block 1002 to generate one or more virtual images of the 4-D computer model of the anatomic structure from the perspective of the virtual camera by perturbing the adjusted pose of the virtual camera. The method then continues to loop through blocks 1002-1007 until the determination in block 1007 is YES.

Figure 11:
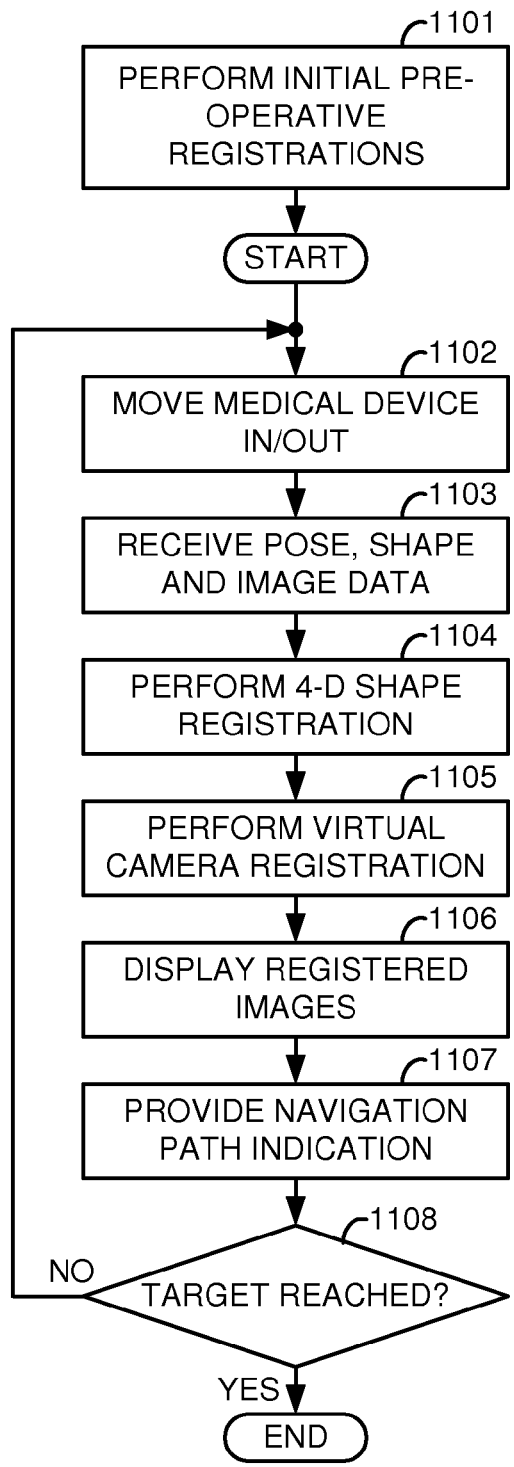
FIG. 11 illustrates a flow diagram of a method for performing a medical procedure including both a first and second method, utilizing aspects of the present invention, for registering a computer model of an anatomical structure with a medical device.

FIG. 11 illustrates, as an example, a flow diagram of a method for performing a medical procedure including both a first and second method for registering a computer model of an anatomical structure with a medical device. In this method, blocks 1101-1103 are performed identically to blocks 801-803 of FIG. 8 and blocks 1106-1108 are performed identically to blocks 805-807 of FIG. 8. Block 1104 is performed identically as the method described in reference to FIG. 9 and may be thought of as a global or coarse registration that is relatively fast to execute. Block 1105 is performed identically to the method described in reference to FIG. 10 and may be thought of as a local or fine registration that corrects for any "residual errors" that may remain after performance of block 1104. Thus, in this example, periodically performing the combination of the methods described in reference to FIGS. 9 and 10 may provide a more accurate registration of the 4-D computer model of the anatomical structure to the medical device 110. Further, periodically performing the global registration of block 1104 may serve to prevent any "drift" errors that may result by only periodically performing block 1105 after an initial registration such as block 801 of FIG. 8.

After performing any of the registration methods described herein, if the resulting virtual image 620 is still visibly misaligned with the captured image 610 (such as viewed on the primary display screen 151), manual registration means may be provided whereby the computer model may be translated and/or oriented according to operator manipulation of an input device until the virtual and captured images appear aligned.

Figure 15:
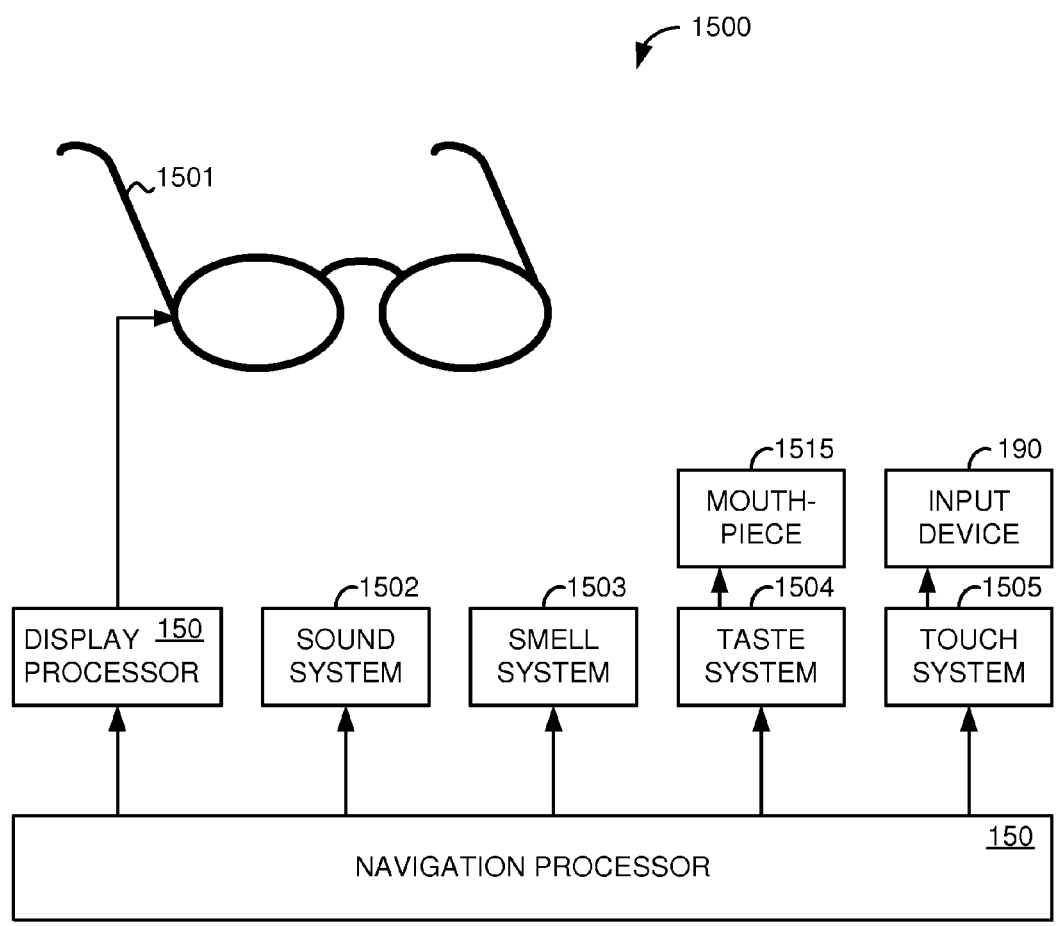
FIG. 15 illustrates a virtual reality system to be optionally used in a medical system utilizing aspects of the present invention.

FIG. 15 illustrates, as an example, a virtual reality system 1500 to be optionally used in the medical system 100 for providing navigation guidance to a surgeon in a virtual reality environment to a target in or adjacent to an anatomical structure in a patient. In the virtual reality system 1500, stereo goggles or glasses 1501, worn by the surgeon, displays either virtual images generated by the virtual camera or real-time images captured by the image capturing element 141 in 3-D as the surgeon moves the medical device 110 through the anatomical structure. As the surgeon approaches each bifurcation in the linked passages of the anatomical structure, an indication of the navigational path to be taken may be provided in one or more of the sense modalities. For example, the navigation processor 160 may perform blocks 801-805 as described in reference to FIG. 8, but in lieu of displaying an arrow in the virtual image 620 on the primary display screen 151, it may provide the navigation indication as an arrow indicating the correct passage to be taken in the stereo glasses 1501 (through the display processor 150) so that the surgeon receives a visual indication of the correct navigational path.

Alternatively or additionally, a navigational path indication may be provided through a sound system 1502 when the medical device 110 approaches a bifurcation by a warning sound being heard if the surgeon directs the distal end 111 of the medical device 110 to enter the wrong passage and/or an assuring sound being heard if the surgeon directs the distal end 111 of the medical device 110 to enter the correct passage. Alternatively or additionally, a navigational path indication may be provided through a smell system 1503 when the medical device 110 approaches a bifurcation by a foul odor being smelt if the surgeon directs the distal end 111 of the medical device 110 to enter the wrong passage and/or pleasing odor being smelt if the surgeon directs the distal end 111 of the medical device 110 to enter the correct passage. Alternatively or additionally, a navigational path indication may be provided through a taste system 1504 when the medical device 110 approaches a bifurcation by a bitter taste being sensed on a mouthpiece 1515 inserted in the surgeon's mouth if the surgeon directs the distal end 111 of the medical device 110 to enter the wrong passage and/or sweet taste being sensed on the mouthpiece 1515 if the surgeon directs the distal end 111 of the medical device 110 to enter the correct passage. Alternatively or additionally, a navigational path indication may be provided through a touch system 1505 when the medical device 110 approaches a bifurcation by a resistive force being felt on the input device 190 if the surgeon directs the distal end 111 of the medical device 110 to enter the wrong passage and/or a forward nudging force being felt on the input device 190 if the surgeon directs the distal end 111 of the medical device 110 to enter the correct passage.

It may be advantageous to determine information of extrema during expansion and contraction cycles of an object, such as an anatomical structure, while performing a procedure on or near the object. For example, an extremum time point such as indicated by the occurrence of an R wave in an electrocardiograph (ECG) signal may be used to augment motion tracking of the heart as described in U.S. Pat. No. 6,858,003 B2 "Performing Cardiac Surgery without Cardioplegia" or the timing of the R wave may be used for triggering the capturing of pre-operative and intra-operative images of the heart so that the pre-operative images may be registered with the intra-operative images at the triggered time points such as described in U.S. Pat. No. 7,398,116 B2 "Methods, Apparatuses, and Systems Useful in Conducting Image Guided Interventions". As yet another example, information of the extrema time points and corresponding determined poses of the object at the limits of its expansion and contraction cycles may be used to interpolate estimated movement of the object at intermediate time points during its expansion and contraction cycles.

Figure 16:
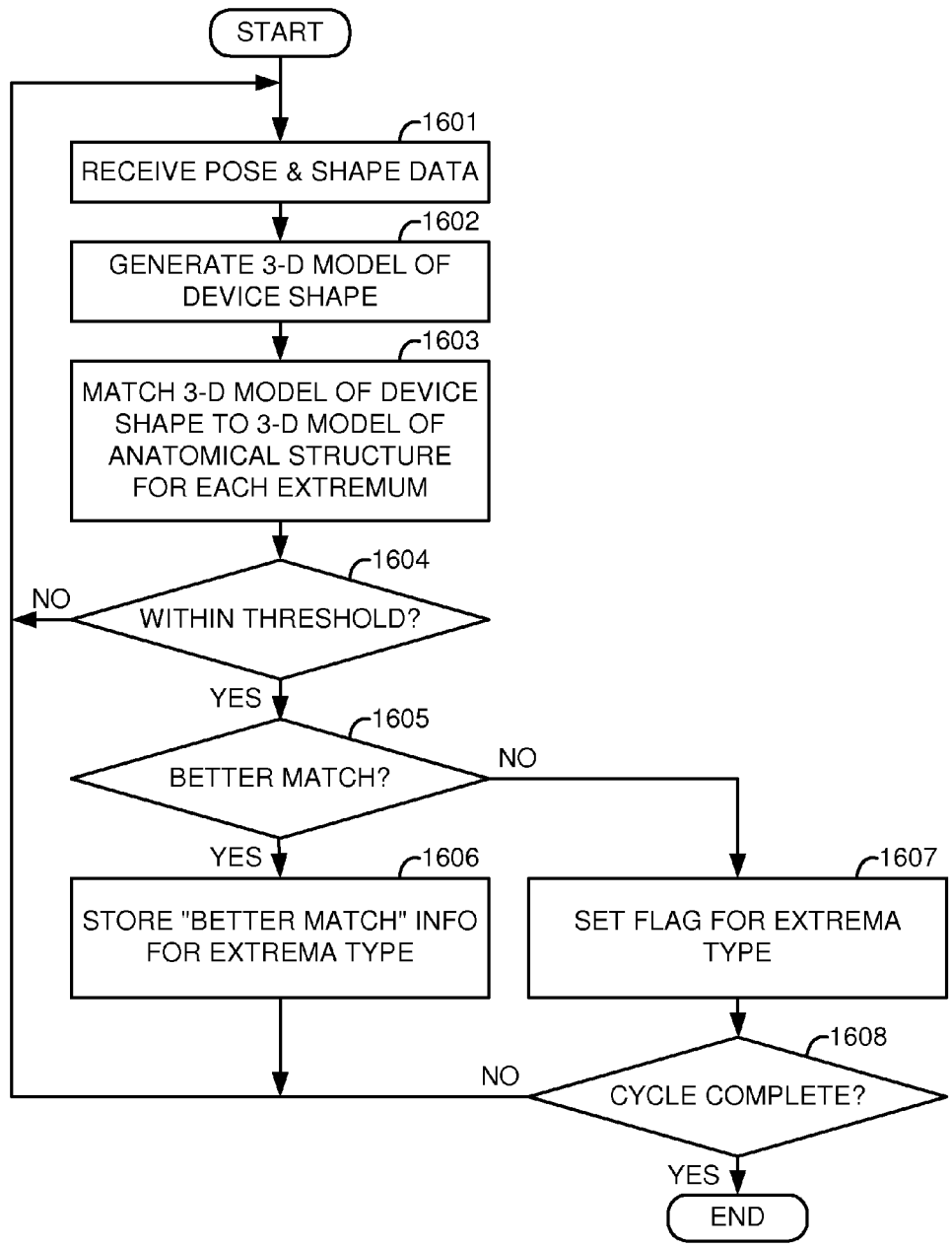
FIG. 16 illustrates a flow diagram of a shape matching method for determining extrema during expansion and contraction cycles of an object.

FIG. 16 illustrates, as an example, a flow diagram of a shape matching method for determining the extrema time points as well as identifying the type of extrema at those time points. This method, as well as other methods described herein, may be performed by one or more of the processors 130, 140, 150, and 160 of FIGS. 1 and 2, alone or in cooperation.

In block 1601, the method receives sampled information for a current process period from a plurality of sensors which are distributed along a length of a flexible device such as the medical device 110 so as to indicate the pose and shape of the flexible device at the time while the flexible device extends through a lumen of the object so as to conform to the shape of the lumen. An example of such arrangement is depicted in FIG. 13, wherein a plurality of sensors, e.g., shape sensors 1310a-1310k, are distributed along the length of the medical device 110, while the medical device 110 extends through a lumen, e.g., passage 1202, of an object, e.g., anatomical structure 1200.

In block 1602, a 3-D computer model corresponding to the current pose and shape of the flexible device is generated using the pose and shape information received, for example, from the pose/shape processor 130. Since the pose and shape information is readily generated from position and shape sensors disposed in the flexible device, a computationally fast determination of the flexible device's pose and shape is made.

In block 1603, the shape of the flexible device is compared against shapes of the linked passages in the 3-D computer model for each extremum type (e.g., maximum inhalation or inspiration and maximum exhalation or expiration when the object is a lung) to determine a measure of how close the shape of the flexible device is to the 3-D model of each extremum type. A number of known matching techniques may be used to perform this function as previously described in reference to block 902 of FIG. 9. Note, however, that instead of comparing the shape of the flexible device with passages of 3-D computer models for all sample times as performed in block 902, only 3-D computer models at the extrema sample times are matched against the flexible device when performing block 1603.

In block 1604, the method determines whether a measure of the closeness of the matching as determined in block 1603 is within a threshold range (e.g., plus or minus a tolerance value about a perfect match value) for the closer match. If the determination in block 1604 is NO, then the method returns to block 1601 to process information for a next process cycle. On the other hand, if the determination in block 1604 is YES, then the method proceeds to block 1605. The threshold range is selected in this case to ensure that correct extrema are detected while not having to waste processing time on instances when the current pose and shape of the flexible device is not near one of the extrema points.

In block 1605, the method determines whether the current pose and shape of the flexible device is a better match than a previously processed match in a prior process cycle to the pose and shape of one of the extrema 3-D models of the object. If it is the first match satisfying block 1604 (i.e., resulting in a YES determination), then it will automatically be the better match. If it is not the first match satisfying block 1604, then it is matched against the "best match to date" for that extremum. As an example, if the current pose and shape of the flexible device is a closer match to the 3-D model of the expiration extremum than it is to the 3-D model of the inspiration extremum, then it will be compared against the "best match to date" with the 3-D model of the expiration extremum. If the determination in block 1605 is YES (i.e., the current pose and shape of the flexible device results in a "better match" with the 3-D model of the extremum), then in block 1606, information of the current pose and shape of the flexible device (including the current time) is stored in a location associated with the extrema type. The method then jumps back to 1601 to process information for the next process cycle. On the other hand, if the determination in block 1605 is NO, then in block 1607, a flag associated with the extrema type is set. The setting of this flag indicates that the "best match" for the 3-D model of the extrema type has been found in the prior determined "best match to date".

In block 1608, the method next determines whether an expansion and contraction cycle for the object has been completed. In the present example, this may be determined by the flags for both extrema types (e.g., inspiration and expiration) being set. If the determination in block 1608 is NO, then the method jumps back to block 1601 to process information for the next process cycle. On the other hand, if the determination in block 1608 is YES, then method ends in block 1609 with the information for each extrema type already stored its associated location in memory by a prior performance of block 1606.

In the methods described so far, it is assumed that a set of 4-D images of an object has been generated over an expansion and contraction cycle of the object, such as described in reference to FIG. 4. Examples of imaging technologies used to generate such images include fluoroscopy, Magnetic Resonance Imaging, thermography, tomography, ultrasound, Optical Coherence Tomography, Thermal Imaging, Impedance Imaging, Laser Imaging, and nano-tube X-ray imaging. Each of which require specialized equipment and set-up time.

In the following methods described in reference to FIGS. 17-21, however, the pre-operative generation of such a set of 4-D images of the object is not required (although if available, information of such may be used). Further, rather than matching the pose and shape of the flexible device against passages of the 3-D models of the object at its extrema, the displacement of a selected point on the flexible device (which is at a fixed insertion length) is tracked relative to a reference point instead, which may significantly speed up the processing and/or use less Central Processing Unit (CPU) time for the determination of the extrema.

The selected point in this case serves as a surrogate to a fixed point on the object which it is approximately adjacent to. Although it does not exactly match movement of the point on the object since the flexible device does not expand and contract as the object expands and contracts, for the purposes of determining the object's extrema in the methods described herein, it serves the purpose. In particular, it is to be appreciated that the position of a point on the lumen (in which the flexible device is disposed) relative to a reference point is approximately the same as and therefore may be determined by determining the position of an adjacent point of the flexible device relative to the reference point, because the flexible device generally fits snugly in the lumen so that the selected point of the lumen and the adjacent point of the flexible device are spatially very close to each other. Further, it is also to be appreciated that as the flexible device is inserted or retracted into or out of the lumen, the specific point on the flexible device (which is adjacent to the point on the lumen) may change, but the new point on the flexible device will be at the same insertion length into the lumen by the flexible device so as to approximate the position of the same point on the object. Thus, as an example, if the flexible device is inserted further into the lumen by 1 unit then the new point being tracked on the flexible device is 1 unit behind the previously tracked point.

Figure 17:
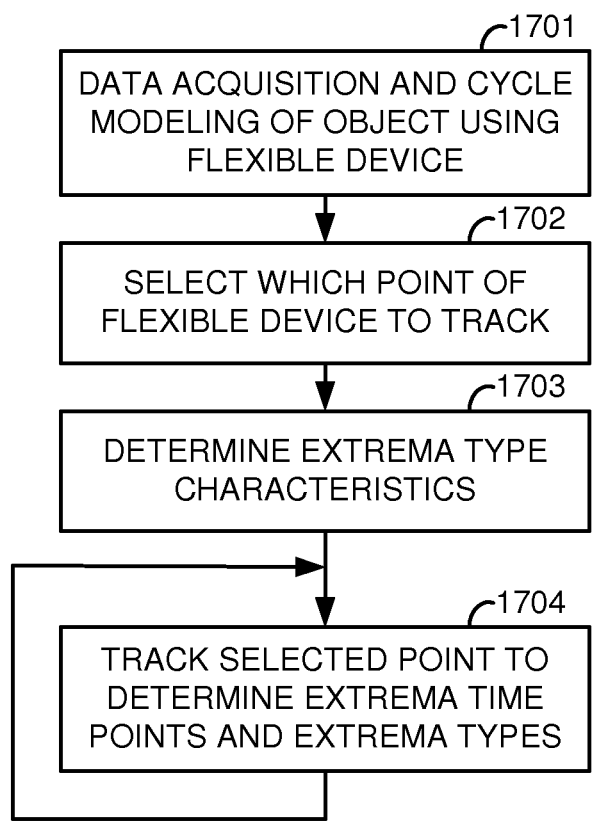
FIG. 17 illustrates a flow diagram of a point tracking method for determining extrema during expansion and contraction cycles of an object.

FIG. 17 illustrates, as an example, a general approach to a point tracking method for determining extrema during an expansion and contraction cycle of an object. In block 1701, a data acquisition and cycle modeling of the object using a flexible device, such as the medical device 110, is performed. In block 1702, a point on the flexible device which is at a fixed insertion length is selected for tracking. In block 1703, characteristics of each extrema type is determined and stored for subsequent processing use. An example of the processing performed in blocks 1701-1703 is provided in FIG. 18. In block 1704, tracking of the selected point is performed to determine extrema time points and identify the extrema type at each of those time points. An example of block 1704 is provided in FIG. 19.

Figure 18:
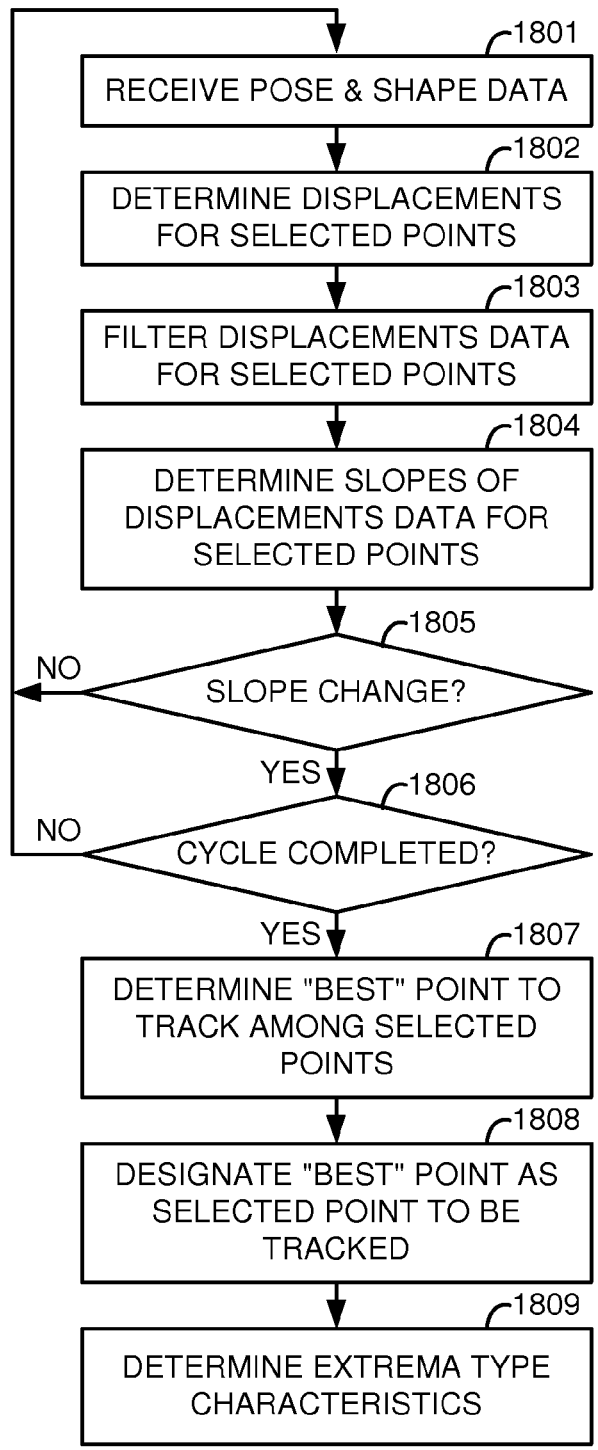
FIG. 18 illustrates a flow diagram of a method for performing a first part of the point tracking method of FIG. 17.

FIG. 18 illustrates, as an example, a flow diagram of a method for performing a first part of the method of FIG. 17, which includes blocks 1701-1703 of FIG. 17. This part of the method may be performed only once before a second part of the method is performed. Alternatively, this part of the method of FIG. 17 may be skipped if the information determined in this first part is provided in some manner such as the operator of the system 100 providing it.

In block 1801, the method receives sampled information for a current process period from a plurality of sensors which are distributed along a length of a flexible device, such as the medical device 110, so as to indicate the pose and shape of the flexible device at the time while the flexible device extends through a lumen of the object so as to conform to the shape of the lumen.

Figure 22A:
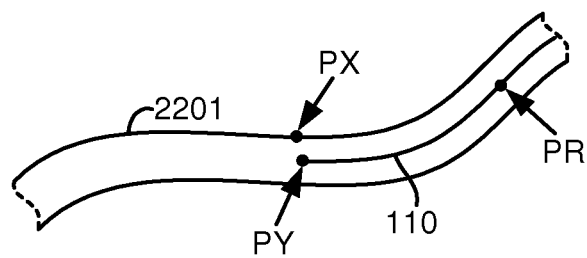
FIGS. 22A-B illustrate simplified cross-sectional views of a flexible medical device disposed within a lumen of an object.
Figure 22B:
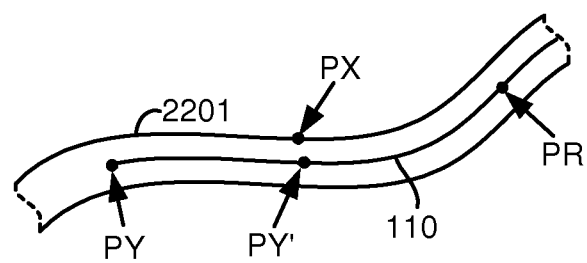

In block 1802, the method determines displacements of a plurality of selected points of the flexible device relative to a reference point PR using the sampled information received from the plurality of sensors. Preferably, the plurality of selected points is evenly distributed along the length of the flexible device although not necessarily one-to-one with the plurality of sensors. Further, the plurality of selected points need not be at the sensor positions. They may be selected at interpolated points between the sensors. The selected points in this case are actually surrogates for points of the lumen to which they are adjacent at the time. So properly speaking, it is actually the points of the lumen that are selected and the so-called selected points of the medical device 110 are actually points of the medical device 110 which happen to be at the time adjacent to the selected points of the lumen. It is to be appreciated that as the lumen moves the selected points of the medical device 110 will approximate the movement of their corresponding lumen points. It is to be further appreciated that the selected points of the medical device 110 are not fixed on physical points of the medical device 110. They are at fixed insertion lengths from the reference point PR. Thus, when the medical device 110 is inserted further into or retracted back out of the lumen, the selected points of the medical device 110 do not follow the movement of the medical device 110. New physical points on the medical device 110 will become the selected points according to the fixed insertion lengths from the reference point PR. As an example, FIG. 22A illustrates a simplified view of the medical device 110 as it is disposed within a lumen 2201 with a physical point PY on the medical device 110 which is adjacent to the selected point PX on the lumen 2201 and at a fixed insertion length that is measured along the length of the medical device 110 from the reference point PR. So that at this time, the physical point PY is designated as the "selected point" on the medical device 110. As the medical device 110 is inserted further into the lumen 2201, however, as shown in FIG. 22B, the physical point PY has moved so that it is no longer adjacent the selected point PX of the lumen 2201. A new physical point PY' of the medical device 110 is now adjacent the selected point PX of the lumen 2201 and at the fixed insertion length. So at this time, the physical point PY' is now designated as the "selected point" on the medical device 110.

Figure 5:
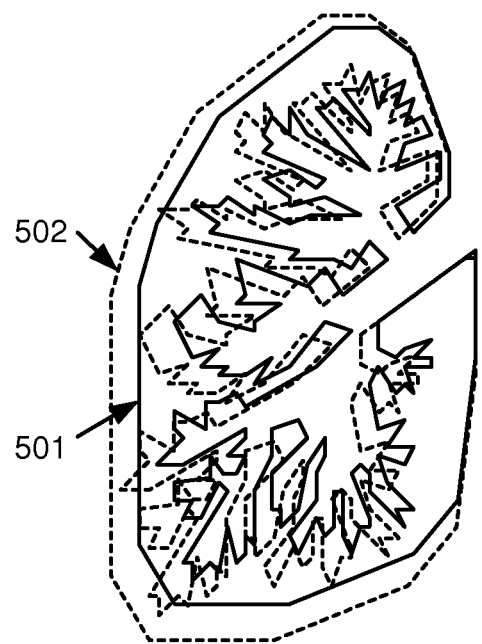
FIG. 5 illustrates movement of a lung during a respiratory cycle.
Figure 20:
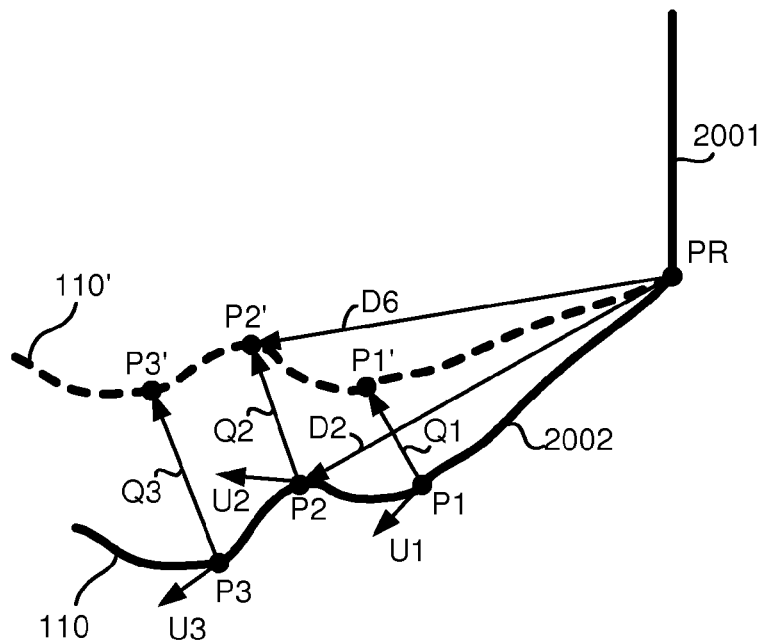
FIG. 20 illustrates movement of a flexible medical device disposed in a passage of a lung during a respiratory cycle.

As an example of a plurality of selected points, referring to FIG. 20, three points P1, P2 and P3 of the medical device 110 may be selected at three different insertion lengths as the medical device 110 is disposed in a passage of the right lung. Movement of the medical device 110 is shown, which results from an expansion and contraction cycle of the lung. The solid line depiction of the medical device 110 indicates its position at full exhalation or contraction of the lung. The dotted line depiction of the medical device 110 (denoted as 110' for differentiation purposes) indicates its position at a full inhalation or expansion of the lung. The medical device 110 comprises two parts—a stationary part 2001 and a moving part 2002. The stationary part 2001 is disposed in the trachea which generally does not move during the respiratory cycle. The moving part 2002, on the other hand, is disposed in the right lung which moves (as depicted in FIG. 5) during the respiratory cycle.

The reference point PR is preferably a point from which the majority of points of the object move away from or towards during expansion and contraction of the object and/or a point which moves less than all points of the object during expansion and contraction cycles of the object. Preferably, the reference point PR is stationary during the expansion and contraction cycle of the object. A user knowledgeable about the relative movements of points of the object during its expansion and retraction may select an appropriate reference point that meets one or both such characteristics. An example of such a reference point for the right or left lung is the main carina of the trachea, which is depicted as reference point 722 in the auxiliary image of the respiratory system illustrated in FIG. 7. One way the user may indicate the reference point PR to the system 100 is to identify the reference point PR on a pre-operative image which is subsequently registered to the patient and medical device 100. Another way is for the user to indicate the reference point PR to the system 100 by identifying it in an auxiliary image of the object such as shown in FIG. 7.

Three alternative methods may be used in block 1802 to determine the displacements.

In the first method, the displacement for each of the points P1, P2 and P3 of the medical device 110 relative to the reference point PR is equal to the magnitude of the vector extending from the reference point PR to the point. For example, the displacement D2 of the point P2 relative to the reference point PR at the expiration extremum is the magnitude of the vector extending from the reference point PR to the point P2 and the displacement D6 of the point P2' relative to the reference point PR at the inspiration extremum is the magnitude of the vector extending from the reference point PR to the point P2'. Mathematically this may be expressed using the following equation (1):

$$P2\ Displacement(t) = Abs(P2(t) - PR) \quad (1)$$

In the second method, the displacement for each of the points P1, P2 and P3 is computed as a relative displacement with respect to their positions at an initial instant of time, thus reducing the dependency on the choice of the reference point PR. For instance, the displacement for point P1' of the medical device relative to its initial position P1 at an arbitrary initial instant of time T0 is equal to the magnitude of the vector difference between the vector extending from P1' to PR and the vector extending from P1 to PR. Such a vector difference is indicated as the vector Q1 in FIG. 20. Mathematically this may be expressed using the following equation (2):

$$P1\ Displacement(t) = Abs(Q1) = Abs((P1'(t) - PR) - (P1(t0) - PR)) \quad (2)$$

In the third method, the displacement for each of the points P1, P2 and P3 is computed as a relative lateral displacement considering both their position at an initial instant of time and the local device pointing direction at the initial instant of time, thus reducing the influence of any motion of sliding or insertion of the device in the expanding and contracting object. For instance, the lateral relative displacement for point P1 is computed by subtracting from the relative displacement vector Q1 its component along the device pointing direction unity vector U1 at point P1 in FIG. 20. Such a component is computed as the scalar product between the vector Q1 and the unity vector U1. Mathematically this may be expressed using the following equation (3):

$$P1\ Displacement(t) = Abs(Q1 - ScalarProduct(Q1, U1)*U1) \quad (3)$$

Figure 21:
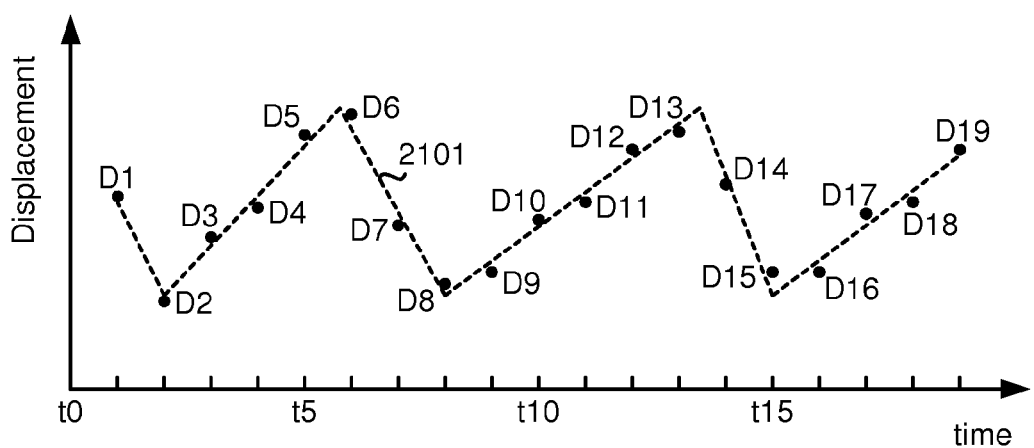
FIG. 21 illustrates displacements of a point of a flexible medical device over time during expansion and contraction cycles of the lung.

In block 1803, the displacements determined in block 1802 optionally may be filtered along with determined displacements of the selected points from prior process periods by the method. For example, FIG. 21 illustrates displacements of the point P2 of the medical device 110 over time during expansion and contraction cycles of the lung. In this example, the displacements D1-D19 have been determined respectively for process periods t1-t19 by the method performing block 1802 in each of those process periods. In practicing the invention, however, it is to be appreciated that more or less process periods may be performed within each expansion and contraction cycle of the lungs depending upon the desired accuracy in determining the extrema time points using the method.

The filtering of the displacement data may be performed using known curve fitting or data smoothing techniques or algorithms. In the present example, a curve 2101 is generated as a saw-tooth pattern by finding a best-fitting line between points of adjacent extrema. More sophisticated higher-order filtering may be performed as well as outliers identified and eliminated before such filtering.

In block 1804, the method determines the slope of the displacement data for each of the selected points. If filtering was performed in block 1803, then the slope is determined at the current process period for each of the curves generated in block 1803. On the other hand, if filtering was skipped by the method skipping block 1803, then the slope may be simply calculated by the difference in displacements of the selected point for the current and immediate prior process periods divided by the time period.

In block 1805, the method determines whether a change in the sign of the slope has occurred between the current and immediately prior process period for any of the selected points. If the determination in block 1805 is NO, then the method jumps back to block 1801 to process information for the next process period. On the other hand, if the determination in block 1805 is YES, then in block 1806, the method determines that an extremum has been encountered and the method proceeds by making a determination whether a complete expansion and contraction cycle has occurred.

One way the method may determine whether an expansion and contraction cycle of the object has completed is to determine whether an extremum of the opposite type has already been detected (e.g., both expansion and contraction limits have been detected) by a slope change determination in an opposite direction. For example, as shown in FIG. 21, if the current process period resulted in a direction change from a plus slope to a negative slope indicating an inspiration limit, then a cycle has been completed if a prior process period resulted in a direction change from a negative slope to a plus slope indicating an expiration limit. Note that in this example, the reference point PR is assumed to be a point from which the selected points move away from during expansion and towards during contraction. If a different reference point PR is chosen such that the selected points move away from during contraction and towards during expansion, then the inspiration and expiration limits would be indicated by opposite slope changes.

If the determination in block 1806 is NO, then the method jumps back to block 1801 to process information for the next process period. On the other hand, if the determination in block 1806 is YES, then in block 1807, the method determines which point of the selected points of the flexible device is a "best" point for tracking purposes. One way for determining which of the selected points should be chosen as the "best" point is to choose the point with the largest displacement from the reference point PR—e.g., the largest displacement D6 of the displacement versus time curves for the selected points P1, P2 and P3. Another way for determining which of the selected points should be chosen as the "best" point in block 1807 is to choose the point with largest displacement between adjacent contraction and expansion states—e.g., the largest displacement among the displacements Q1, Q2 and Q3 in FIG. 20.

In block 1808, the method then designates the "best" point as the selected point of the flexible device to be tracked.

In block 1809, the method determines extrema characteristics for the extremum detected in block 1805. The extremum type may be determined, for example, by the direction of the slope change detected in block 1805. Typically, the reference point is selected so that the displacement of the selected point is larger at the inspiration extremum than the displacement of the selected point at the expiration extremum. As a result, at an expiration extremum (such as occurring at time t2), the slope changes from a negative slope to a positive slope. Conversely, at an inspiration extremum (such as occurring at time t6), the slope changes from a positive slope to a negative slope. Thus, one example of an extrema characteristic is the direction of the slope change at the extremum.

Another example of an extrema characteristic is the displacement of the selected point at the detected extremum. Still another example of an extrema characteristic is the amount of time spent near the extremum for an average expansion and contraction cycle. For example, in the lungs, much more time is spent in the exhalation state, and relatively little time is spent in the inhalation state, so that the extremum type may also be determined by the amount of time spent at near the extremum. Yet another example of an extrema characteristic is the 3-D model of the object at the extremum (if available).

Figure 19:
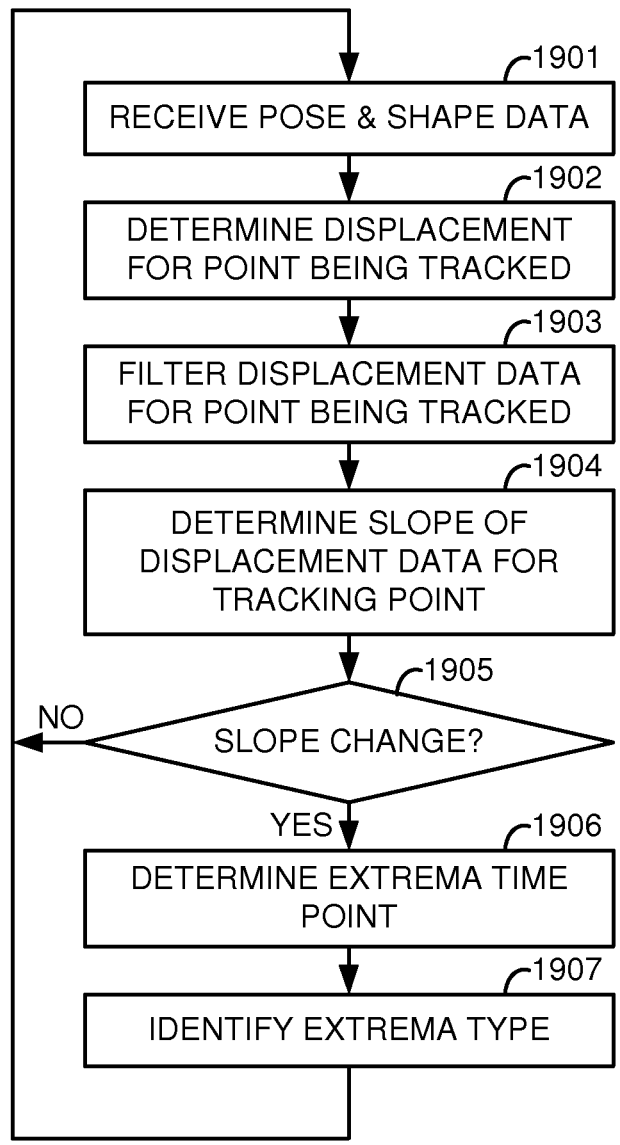
FIG. 19 illustrates a flow diagram of a method for performing a second part of the point tracking method of FIG. 17.

FIG. 19 illustrates, as an example, a flow diagram of a method for performing a second part of the method of FIG. 17, which includes block 1704 of FIG. 17. This part of the method is continuously performed as long as information of the extrema is being determined.

In block 1901, the method receives sampled information for a current process period from a plurality of sensors which are distributed along a length of a flexible device, such as the medical device 110, so as to indicate the pose and shape of the flexible device at the time while the flexible device extends through a lumen of the object so as to conform to the shape of the lumen. An example of such is depicted in FIG. 13, wherein a plurality of sensors, e.g., shape sensors 1310a-1310k, are distributed along the length of a flexible device, e.g., medical device 110, while the flexible device extends through a lumen, e.g., passage 1202, of an object, e.g., anatomical structure 1200. Using this information, the method determines the pose of the point selected for tracking in block 1808 of FIG. 18.

In block 1902, the method determines a displacement of the selected point of the flexible device relative to a reference point using the sampled information received from the plurality of sensors in a similar manner as described in reference to block 1802 of FIG. 18.

In block 1903, the displacement determined in block 1602 is optionally filtered along with determined displacements of the selected point from prior process periods by the method in a similar manner as described in reference to block 1803 of FIG. 18.

In block 1904, the slope of the displacement data of the selected point is determined by the method. If the optional filtering was performed in block 1903, then the slope is determined at the current process period for the curve generated in block 1903. On the other hand, if filtering was skipped by the method skipping block 1903, then the slope may be simply calculated by the difference in displacements of the selected point for the current and immediate prior process periods divided by the time period.

In block 1905, the method determines whether a change in the sign of the slope has occurred between the current and immediately prior process period. If the determination in block 1905 is NO, then the method jumps back to block 1901 to process information for the next process cycle. On the other hand, if the determination in block 1905 is YES, then in block 1906, the method determines that an extremum has been detected and that the current time is the extremum's time point.

In block 1907, the method next determines the type of extremum using one or more of the extrema characteristics determined in block 1809 of FIG. 18. For example, if the slope changes from a negative slope to a positive slope, then the method determines that the extremum type is an expiration, such as occurs for displacements D2, D8 and D15 of FIG. 21. On the other hand, if the slope changes from a positive slope to a negative slope, then the method determines that the extremum type is an inspiration, such as occurs for displacements D6, D13 and D19 of FIG. 21. As another example, the displacement of the selected point at the detected extremum may be compared with displacements for the inspiration and expiration extrema to determine whether it corresponds to one or the other. As another example, the amount of time spent near the detected extremum may be compared with those for an average expansion and contraction cycle to determine whether it is one or the other. As still another example, the current pose and shape of the flexible device at the detected extremum may be compared with 3-D models of the object at the extrema (if available) to determine whether it corresponds to one or the other.

The method then records both the extremum type (e.g., expiration or inspiration) and time point of the detected extremum in memory 161 for various uses such as those described earlier, and jumps back to block 1901 to process information for the next process period.

Although the various aspects of the present invention have been described with respect to one or more embodiments, it will be understood that the invention is entitled to full protection within the full scope of the appended claims.

What is claimed is:

1. A method for determining information of extrema during expansion and contraction cycles of an object, the method comprising:
   receiving time sampled information from a plurality of sensors distributed along a length of a flexible device so as to indicate the shape of the flexible device over time while the flexible device extends through a lumen of the object so as to conform to and resemble the shape of the lumen;
   determining displacements over time of a selected point at a selected insertion length of the flexible device into the lumen of the object relative to a reference point using the time sampled information received from the plurality of sensors;
   determining extrema time points during the expansion and contraction cycles of the object by identifying sign changes of the slope of the determined displacements of the point of the lumen over time; and
   identifying extrema types during the expansion and contraction cycles of the object by using extrema type characteristics.

2. The method of claim 1, wherein the plurality of sensors include strain sensors configured on an optical fiber extending along the length of the flexible device.

3. The method of claim 1, wherein the determination of the displacements over time of the selected point comprises periodically:
   determining a vector from the reference point to the pose of the selected point at each point in time; and
   determining the displacement of the selected point by calculating the magnitude of the determined vector.

4. The method of claim 1, wherein the determination of the displacements over time of the selected point comprises determining a second vector from the reference point to the pose of the selected point at an initial point of time and periodically:

determining a first vector from the reference point to the pose of the selected point;
determining a first difference vector between the first vector and the second vector; and
determining the displacement of the selected point by calculating the magnitude of the determined first difference vector.

5. The method of claim 4, wherein the determination of the displacements over time of the selected point further comprises determining a unit vector indicating the pointing direction of the flexible device at the initial point of time at the selected point from a plurality of sensors distributed along a length of the flexible device and periodically:
determining a scalar product of the first vector difference and the unit vector;
determining a second vector difference between the first vector and the unit vector multiplied by the scalar product; and
determining the displacement of the selected point by calculating the magnitude of the second vector difference.

6. The method of claim 1, wherein the reference point is a point from which points of the object move away from during expansion of the object.

7. The method of claim 1, wherein the reference point is a point which moves less than all points of the object during expansion and contraction cycles of the object.

8. The method of claim 1, wherein the determination of the extrema time points during expansion and contraction of the object over time comprises:
filtering the determined displacements of the point of the lumen over time; and
determining changes in the sign of the slope of the filtered determined displacements of the point of the lumen over time.

9. The method of claim 8, wherein the filtering of the determined displacements of the selected point over time comprises:
determining a curve that best fits through the determined displacements of the selected point over time.

10. The method of claim 1, wherein the object is an anatomical structure within a patient.

11. The method of claim 10, wherein the anatomical structure is a lung and the lumen comprises one or more of a trachea, bronchi, bronchioles, and artificial passages.

12. The method of claim 11, wherein the reference point is a point on an adjacent object that is stationary with respect to the expansion and contraction movement of the object.

13. The method of claim 10, wherein the anatomical structure is one of a heart, brain, digestive system, circulatory system, and urinary system.

14. The method of claim 1, wherein the flexible device includes one of an endoscope, a catheter, and a medical instrument.

15. The method of claim 1, wherein the expansion and contraction of the object is associated with a circulation through the object of at least one of air and blood.

16. The method of claim 1, wherein the selected point of the flexible device is selected by determining which point of a plurality of selected points of the flexible device has the largest determined displacement relative to the reference point over an expansion and contraction cycle of the object.

17. The method of claim 1, wherein the selected point of the flexible device is selected by determining which point of a plurality of selected points of the flexible device has a largest displacement between positions of adjacent extrema over an expansion and contraction cycle of the object.

18. The method of claim 1, wherein the extrema type characteristics include sign changes for a slope of the displacements over time of the selected point, and wherein the identifying of the extrema types during expansion and contraction cycles of the object comprise identifying a first extrema type if the sign of the slope changes from positive to negative and identifying a second extrema type if the sign of the slope changes from n.

19. The method of claim 1, wherein the extrema type characteristics include expected displacements of the selected point at the extrema, and wherein the identifying of the extrema types during expansion and contraction cycles of the object comprise identifying the extrema type by comparing the current displacement of the selected point with the expected displacements of the selected point at the extrema.

20. The method of claim 1, wherein the extrema type characteristics include expected times spent near the extrema, and wherein the identifying of the extrema types during expansion and contraction cycles of the object comprise comparing the time spent near a detected extremum with the expected times spent near the extrema.

21. The method of claim 1, wherein the extrema type characteristics include 3-D computer models of the object at the extrema, and wherein the identifying of the extrema types during expansion and contraction cycles of the object comprise comparing a current shape of the flexible device with lumens of the 3-D computer models of the object at the extrema.

22. A system comprising:
a flexible device including a plurality of sensors distributed along a length of the flexible device so as to indicate the shape of the flexible device as the flexible device extends through a lumen of an object so as to conform to and resemble the shape of the lumen; and
one or more processors adapted to determine information of extrema during expansion and contraction cycles of the object by receiving time sampled information from the plurality of sensors, determine displacements over time of a selected point at a selected insertion length of the flexible device into the lumen of the object relative to a reference point using the time sampled information received from the plurality of sensors, determine the extrema time points during the expansion and contraction of the object over time by identifying changes in the sign of the slope of the determined displacements of the point over time, and identify extrema types during the expansion and contraction cycles of the object by using extrema type characteristics.

23. The system of claim 22, wherein the plurality of sensors include strain sensors configured on an optical fiber extending along the length of the flexible device.

24. The system of claim 22, wherein the one or more processors is adapted to determine the displacements over time of the selected point by periodically: determining a vector from the reference point to the pose of the selected point at each point in time; determine the displacement of the selected point by calculating the magnitude of the determined vector.

25. The system of claim 22, wherein the one or more processors is adapted to determine the displacements over time of the selected point by determining a second vector from the reference point to the pose of the selected point at an initial point of time and periodically: determining a first vector from the reference point to the pose of the selected point; determining a first difference vector between the first vector and the second vector; and determining the displacement of the selected point by calculating the magnitude of the determined first difference vector.

26. The system of claim 25, wherein the one or more processors is adapted to determine the displacements over time of the selected point by further determining a unit vector indicating the pointing direction of the flexible device at the initial point of time at the selected point from a plurality of sensors distributed along a length of the flexible device and periodically: determining a scalar product of the first vector difference and the unit vector; determining a second vector difference between the first vector and the unit vector multiplied by the scalar product; and determining the displacement of the selected point by calculating the magnitude of the second vector difference.

27. The system of claim 22, wherein the reference point is a point from which points of the object move away from during expansion of the object.

28. The system of claim 22, wherein the reference point is a point which moves less than all points of the object during expansion and contraction cycles of the object.

29. The system of claim 22, wherein the one or more processors is adapted to determine the extrema time points during expansion and contraction of the object over time by filtering the determined displacements of the point of the lumen over time and determining changes in the sign of the slope of the filtered determined displacements of the point of the lumen over time.

30. The system of claim 29, wherein the one or more processors is adapted to filter the determined displacements of the selected point over time by determining a curve that best fits through the determined displacements of the selected point over time.

31. The system of claim 22, wherein the object is an anatomical structure within a patient.

32. The system of claim 31, wherein the anatomical structure is a lung and the lumen comprises one or more of a trachea, bronchi, bronchioles, and artificial passages.

33. The system of claim 32, wherein the reference point is a point adjacent to the object that is stationary with respect to the expansion and contraction movement of the object.

34. The system of claim 31, wherein the anatomical structure is one of a heart, brain, digestive system, circulatory system, and urinary system.

35. The system of claim 22, wherein the flexible device includes one of an endoscope, a catheter, and a medical instrument.

36. The system of claim 22, wherein the expansion and contraction of the object is associated with a circulation through the object of at least one of air and blood.

37. The system of claim 22, wherein the one or more processors is adapted to select the selected point of the flexible device by determining which point of a plurality of selected points of the flexible device has the largest determined displacement relative to the reference point over an expansion and contraction cycle of the object.

38. The system of claim 22, wherein the one or more processors is adapted to select the selected point of the flexible device by determining which point of a plurality of selected points of the flexible device has a largest displacement between positions of adjacent extrema over an expansion and contraction cycle of the object.

39. The system of claim 22, wherein the extrema type characteristics include sign changes for a slope of the displacements over time of the selected point, and wherein the one or more processors is adapted to identify the extrema types during expansion and contraction cycles of the object by identifying a first extrema type if the sign of the slope changes from positive to negative and identifying a second extrema type if the sign of the slope changes from negative to positive.

40. The system of claim 22, wherein the extrema type characteristics include expected displacements of the selected point at the extrema, and wherein the one or more processors is adapted to identify the extrema types during expansion and contraction cycles of the object by comparing the current displacement of the selected point with the expected displacements of the selected point at the extrema.

41. The system of claim 22, wherein the extrema type characteristics include expected times spent near the extrema, and wherein the one or more processors is adapted to identify the extrema types during expansion and contraction cycles of the object by comparing the time spent near a detected extremum with the expected times spent near the extrema.

42. The system of claim 22, wherein the extrema type characteristics include 3-D computer models of the object at the extrema, and wherein the one or more processors is adapted to identify the extrema types during expansion and contraction cycles of the object by comparing a current shape of the flexible device with lumens of the 3-D computer models of the object at the extrema.

* * * * *